United States Patent [19]

Teranishi et al.

[11] 4,410,528

[45] Oct. 18, 1983

[54] HYPOTENSIVE PIPERIDINE DERIVATIVES

[75] Inventors: Masayuki Teranishi; Hiroyuki Obase; Nobuhiro Nakamizo, all of Machida, Japan; Kazuhiro Kubo, Berchem, Belgium; Yutaka Kasuya, Kanagawa, Japan

[73] Assignee: Kyowa Hakko Kogyo Co., Ltd., Tokyo, Japan

[21] Appl. No.: 264,810

[22] Filed: May 18, 1981

[30] Foreign Application Priority Data

May 16, 1980 [JP] Japan ................................. 55-65094
May 21, 1980 [JP] Japan ................................. 55-66531
May 21, 1980 [JP] Japan ................................. 55-66532
Aug. 22, 1980 [JP] Japan ................................. 55-114759

[51] Int. Cl.$^3$ .................... A61K 31/505; C07D 401/04
[52] U.S. Cl. ..................................... 424/251; 424/267; 544/292; 546/197; 546/199; 546/201
[58] Field of Search ................... 546/197, 199, 201; 544/292; 424/251, 267

[56] References Cited

U.S. PATENT DOCUMENTS 4,224,333 9/1980 Clemence et al. ............... 546/201 X

FOREIGN PATENT DOCUMENTS 925429 5/1963 United Kingdom ............... 546/201
1404003 8/1975 United Kingdom ............... 546/201

*Primary Examiner*—Richard A. Schwartz
*Attorney, Agent, or Firm*—Antonelli, Terry & Wands

[57] ABSTRACT

A new piperidine derivative represented by the formula:

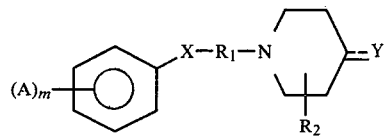

wherein X is oxygen, sulfur, carbonyl, hydroxymethylene or methylene; $R_1$ is straight-chain alkylene having 1-4 carbon atoms with or without lower alkyl substituent(s); $(A)_m$ and $R_2$ are usually used substituents; and Y is a monovalent group or a divalent group and is one of the following three groups:

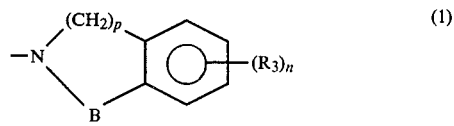

wherein when p is 0, B is —N=N—,

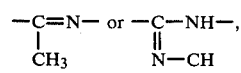

and when p is 1, B is

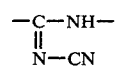

wherein $(R_3)_n$ is a usually used substituent, has hypotensive activity.

4 Claims, No Drawings

HYPOTENSIVE PIPERIDINE DERIVATIVES

The present invention relates to novel piperidine derivatives, acid addition salts thereof and pharmaceutical compositions containing the derivatives or acid addition salts thereof.

The piperidine derivatives are compounds represented by the formula [I]:

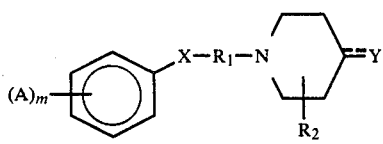

[I]

wherein A is hydroxy, halogen, lower alkyl, lower alkoxy, lower alkenyloxy, lower alkynyloxy, lower alkylthio, carboxy, lower alkoxycarbonyl, nitro, amino, lower alkylamino, lower alkanoylamino, sulfamoyl, mono- or di-lower alkylaminosulfonyl, lower alkylsulfonyl, carbamoyl, cyano or trifluoromethyl, m is 0 or an integer of 1-5 and when m is 2 or more, each A is the same group or each A is a different group and A has the same definition as defined above or two A groups may combine to form a lower alkylenedioxy; X is oxygen, sulfur, carbonyl, hydroxymethylene or methylene; $R_1$ is straight-chain alkylene having 1-4 carbon atoms with or without lower alkyl substituent(s); $R_2$ is hydrogen or lower alkyl; and Y is a monovalent group or a divalent group and is one of the following three groups:

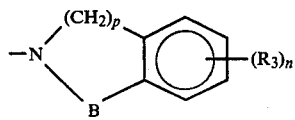

(1)

wherein p is 0 or 1, B is —N=N—,

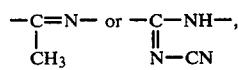

when p is 0, B is —N=M—,

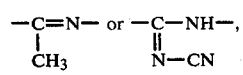

and when p is 1, B is

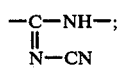

and $R_3$ is hydroxy, lower alkoxy, halogen, trifluoromethyl, trifluoromethoxy, trifluoromethylthio, nitro or amino, n is 0 or an integer of 1-4, and when n is 2 or more, each $R_3$ is the same group or each $R_3$ is a different group and has the same definition as defined above or two $R_3$ groups may combine to form a lower alkylenedioxy

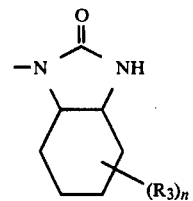

(2)

wherein $R_3$ and n have the same definitions as defined above and

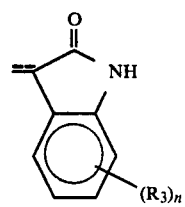

(3)

wherein $R_3$ and n have the same definitions as defined above.

The compounds represented by the formula [I] and the pharmaceutically acceptable acid addition salts thereof have a hypotensive activity, and therefore are useful as medicine.

Heretofore, the following compounds, each having a piperidine ring, are commercially available as tranquilizers.

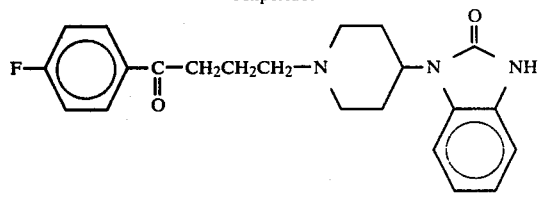

benperidol

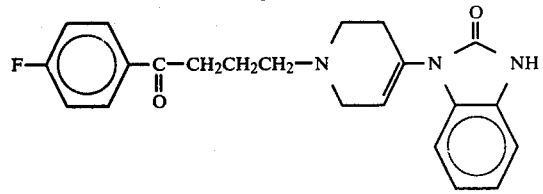

droperidol

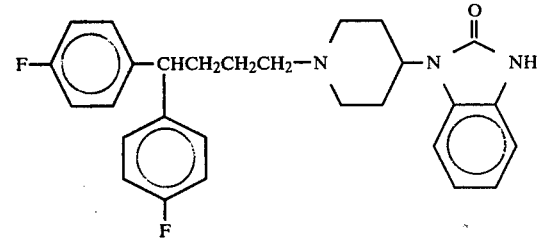

pimozide

Further, Japanese Published Patent Application No. 160371/1979 and WO 80/00024 published on Jan. 10, 1980 disclose piperidine derivatives having a hypotensive activity. Representative piperidine derivatives are represented by the following formula:

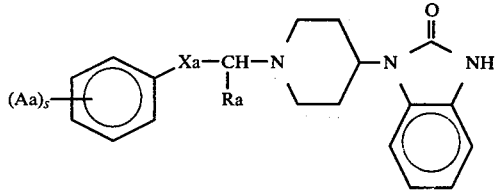

(wherein Aa is methoxy or two Aa groups may combine to form methylenedioxy; s is 0 or an integer of 1-3; Xa is carbonyl, hydroxymethylene or methylene; and Ra is hydrogen or methyl). A U.S. application based on the PCT application is pending (U.S. Pat. Application Ser. No. 191,339 filed on Jan. 31, 1980).

Further, piperidine derivatives having a hypotensive activity are disclosed in U.S. patent application Ser. Nos. 209,284 and 241,727, respectively, filed on Nov. 21, 1980 and Mar. 9, 1981.

Some of the inventors of the above applications are common with the present invention.

Compounds having excellent pharmacological activities are always in demand. In order to obtain such compounds, studies have been made on piperidine derivatives and as a result, it has been found that novel piperidine derivatives represented by the formula [I] have various pharmacological activities, especially a hypotensive activity.

The present invention relates to the compounds represented by the above formula [I] (hereinafter referred to as Compound [I] and terms like this shall apply to other compounds), acid addition salts thereof and their use as medicine.

Halogen in the definition of A and $R_3$ in Compound [I] includes chlorine, bromine, etc. The term "lower" in the definition of the various groups in Compound [I] means having 1-5 carbon atoms, especially 1-3, except for "lower alkoxycarbonyl" which has 2-6 carbon atoms, especially 2-4.

Compound [I] includes all of the optical isomers.

Examples of pharmacologically acceptable acid addition salts of Compound [I] are inorganic acid addition salts such as hydrochloride, hydrobromide, hydroiodide, nitrate, sulfate and phosphate, and organic acid addition salts such as acetate, benzoate, maleate, fumarate, succinate, tartrate, citrate, oxalate, glyoxylate, aspartate, methanesulfonate, ethanesulfonate, propanesulfonate, methanedisulfonate, α,β-ethanedisulfonate and benzenesulfonate.

Especially preferable compounds in Compound [I] are represented by the formula [I']:

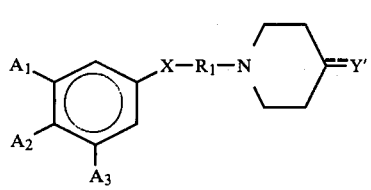

[I']

wherein $A_1$, $A_2$ and $A_3$ each are the same group or are each a different group, and $A_1$, $A_2$ and $A_3$ are hydrogen or have the same definitions as that of the above-mentioned A group in Formula [1]; X and $R_1$ have the same definitions as defined in Formula (2); and Y' is a monovalent group or a divalent group and is one of the following three groups:

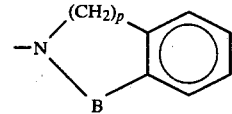

(1)

wherein p and B have the same definitions as defined in Formula [I].

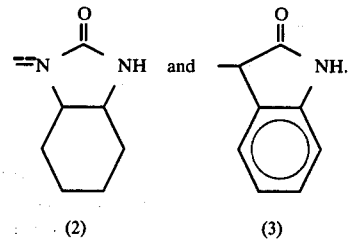

(2)      (3)

Examples of Compound [I] are tabulated in the following Table 1. Table 2 shows structures and Tables 3-1, 3-2 and 3-3 show properties of the present compounds.

TABLE 1

| Compound No. | Compound |
|---|---|
| 1 | 1-[2-(3,4-methylenedioxyphenyl)-2-oxo-ethyl]-4-(1H—benzotriazol-1-yl)piperidine |
| 2 | 1-[2-(3,4-dimethoxyphenyl)-2-oxo-ethyl]-4-(1H—benzotriazol-1-yl)piperidine |
| 3 | 1-[1-(3,4-dimethoxybenzoyl)ethyl]-4-(1H—benzotriazol-1-yl)piperidine |
| 4 | 1-[2-(3,4-methylenedioxyphenyl)-2-hydroxy-ethyl]-4-(1H—benzotriazol-1-yl)piperidine |
| 5 | 1-[2-(3,4-dimethoxyphenyl)-2-hydroxy-ethyl]-4-(1H—benzotriazol-1-yl)piperidine |
| 6 | 1-[3-(3,4-dimethoxyphenyl)-3-hydroxypropyl-2]-4-(1H—benzotriazol-1-yl)piperidine |
| 7 | 1-[2-(3,4-methylenedioxyphenyl)-2-oxo-ethyl]-4-(2-methyl-benzimidazol-3-yl)piperidine |
| 8 | 1-[2-(3,4-dimethoxyphenyl)-2-oxo-ethyl]-4-(2-methyl-benzimidazol-3-yl)piperidine |
| 9 | 1-[1-(3,4-dimethoxybenzoyl)ethyl]-4-(2-methyl-benzimidazol-3-yl)piperidine |
| 10 | 1-[2-(3,4-methylenedioxyphenyl)-2-hydroxy-ethyl]-4-(2-methyl-benzimidazol-3-yl)piperidine |
| 11 | 1-[2-(3,4-dimethoxyphenyl)-2-hydroxyethyl]-4-(2-methyl-benzimidazol-3-yl)piperidine |
| 12 | 1-[3-(3,4-dimethoxyphenyl)-3-hydroxypropyl-2-]-4-(2-methyl-benzimidazol-3-yl)piperidine |
| 13 | 1-(3,4-methylenedioxybenzoylmethyl)-4-(2-cyanoimino-3,4-dihydro-1H—quinazolin-3-yl)piperidine |
| 14 | 1-(3,4-dimethoxybenzoylmethyl)-4-(2-cyanoimino-3,4-dihydro-1H—quinazolin-3-yl)piperidine |
| 15 | 1-[2-(3,4-dimethoxyphenyl)-2-oxo-1-methyl-ethyl]-4-(2-cyanoimino-3,4-dihydro-1H—quinazolin-3-yl)piperidine |
| 16 | 1-(3,4,5-trimethoxybenzoylmethyl)-4-(2-cyanoimino-3,4-dihydro-1H—quinazolin-3-yl)piperidine |
| 17 | 1-[2-(3,4,5-trimethoxyphenyl)-2-oxo-1-methyl-ethyl]-4-(2-cyanoimino-3,4-dihydro-1H—quinazolin-3-yl)piperidine |
| 18 | 1-[2-(3,4-methylenedioxyphenyl)-2-oxo-ethyl]-4-(2-cyanoimino-1H—benzimidazol-1-yl)piperidine |
| 19 | 1-[2-(3,4-dimethoxyphenyl)-2-oxo-ethyl] -4-(2-cyanoimino-1H—benzimidazol-1-yl)piperidine |
| 20 | 1-[2-(3,4-methylenedioxyphenyl)-2-hydroxy-ethyl]-4-(2-cyanoimino-3,4-dihydro-1H—quinazolin-3-yl)piperidine |

TABLE 1-continued

| Compound No. | Compound |
|---|---|
| 21 | 1-[2-(3,4-dimethoxyphenyl)-2-hydroxy-ethyl]-4-(2-cyanoimino-3,4-dihydro-1H—quinazolin-3-yl)piperidine |
| 22 | 1-[2-(3,4-dimethoxyphenyl)-2-hydroxy-1-methyl-ethyl]-4-(2-cyanoimino-3,4-dihydro-1H—quinazolin-3-yl)piperidine |
| 23 | 1-[2-(3,4,5-trimethoxyphenyl)-2-hydroxy-ethyl]-4-(2-cyanoimino-3,4-dihydro-1H—quinazolin-3-yl)piperidine |
| 24 | 1-[2-(3,4,5-trimethoxyphenyl)-2-hydroxy-1-methyl-ethyl]-4-(2-cyanoimino-3,4-dihydro-1H—quinazolin-3-yl)piperidine |
| 25 | 1-[2-(3,4-methylenedioxyphenyl)-2-hydroxy-ethyl]-4-(2-cyanoimino-1H—benzimidazol-1-yl)piperidine |
| 26 | 1-[2-(3,4-dimethoxyphenyl)-2-hydroxy-ethyl]-4-(2-cyanoimino-1H—benzimidazol-1-yl)piperidine |
| 27 | 1-[(3,4-methylenedioxy)benzoylmethyl]-4-(2-oxyindol-3-yl)piperidine |
| 28 | 1-[(3,4-dimethoxy)benzoylmethyl]-4-(2-oxyindol-3-yl)piperidine |
| 29 | 1-[2-(3,4-dimethoxyphenyl)-2-oxo-1-methyl-ethyl]-4-(2-oxyindol-3-yl)piperidine |
| 30 | 3-[1-(3,4-methylenedioxy)benzoylmethyl-4-piperidylidene]-2-oxyindole |
| 31 | 3-[1-(3,4-dimethoxy)benzoylmethyl-4-piperidylidene]-2-oxyindole |
| 32 | 1-[2-(3,4-methylenedioxyphenyl)-hydroxyethyl]-4-(2-oxyindol-3-yl)piperidine |
| 33 | 1-[2-(3,4-dimethoxyphenyl)-hydroxyethyl]-4-(2-oxyindol-3-yl)piperidine |
| 34 | 1-[2-(3,4-dimethoxyphenyl)-2-hydroxy-1-methyl-ethyl]-4-(2-oxyindol-3-yl)piperidine |
| 35 | 3-{1-[2-(3,4-methylenedioxyphenyl)-2-hydroxyethyl]-4-piperidylidene}-2-oxyindole |
| 36 | 3-{1-[2-(3,4-dimethoxyphenyl)-2-hydroxyethyl]-4-piperidylidene}-2-oxyindole |
| 37 | 1-[2-(3,4-dimethoxyphenyl)-2-oxoethyl]-4-(octahydro-2H—benzimidazol-2-one-1-yl)piperidine |
| 38 | 1-[2-(3,4-dimethoxyphenyl)-2-oxo-1-methylethyl]-4-(octahydro-2H—benzimidazol-2-one-1-yl)piperidine |
| 39 | 1-[1-(3,4,5-trimethoxybenzoyl)ethyl]-4-(octahydro-2H—benzimidazol-2-one-1-yl)piperidine |
| 40 | 1-[2-(3,4,5-trimethoxyphenyl)-2-oxo-ethyl]-4-(octahydro-2H—benzimidazol-2-one-1-yl)piperidine |
| 41 | 1-[2-(3,4-dimethoxyphenyl)-2-hydroxyethyl]-4-(octahydro-2H—benzimidazol-2-one-1-yl)piperidine |
| 42 | 1-[2-(3,4-dimethoxyphenyl)-2-hydroxy-1-methylethyl]-4-(octahydro-2H—benzimidazol-2-one-1-yl)piperidine |
| 43 | 1-[2-(3,4,5-trimethoxyphenyl)-2-hydroxy-1-methylethyl]-4-(octahydro-2H—benzimidazol-2-one-1-yl)piperidine |
| 44 | 1-[2-(3,4,5-trimethoxyphenyl)-2-hydroxyethyl]-4-(octahydro-2H—benzimidazol-2-one-1-yl)piperidine |

TABLE 2

Structure of compound

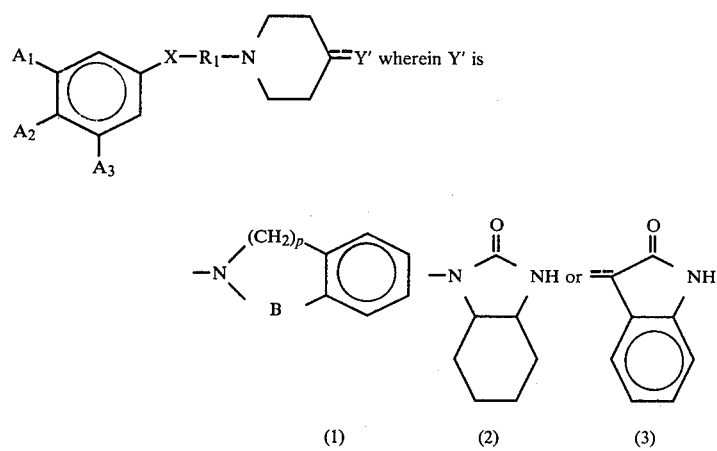

| Compound No. | A₁ | A₂ | A₃ | X | R₁ | Y' | B | p |
|---|---|---|---|---|---|---|---|---|
| 1 | —O—CH₂—O— (3,4-methylenedioxy) | | H | —C(=O)— | —CH₂— | (1) | —N=N— | 0 |
| 2 | OMe | OMe | H | —C(=O)— | —CH₂— | (1) | —N=N— | 0 |
| 3 | OMe | OMe | H | —C(=O)— | —CH(Me)— | (1) | —N=N— | 0 |

TABLE 2-continued

Structure of compound $$A_1, A_2, A_3\text{-phenyl}-X-R_1-N\text{-piperidine}=Y' \text{ wherein } Y' \text{ is}$$

(1) $-N((CH_2)_p\text{-phenyl-B})$-

(2) $-N$-(hexahydrobenzimidazol-2-one)-NH (3) 3-(indolin-2-one)

| Compound No. | A₁ | A₂ | A₃ | X | R₁ | Y' | B | p |
|---|---|---|---|---|---|---|---|---|
| 4 | —O—CH₂—O— | | H | —CH(OH)— | —CH₂— | (1) | —N=N— | 0 |
| 5 | OMe | OMe | H | —CH(OH)— | —CH₂— | (1) | —N=N— | 0 |
| 6 | OMe | OMe | H | —CH(OH)— | —CH(Me)— | (1) | —N=N— | 0 |
| 7 | —O—CH₂—O— | | H | —C(=O)— | —CH₂— | (1) | —C(Me)=N— | 0 |
| 8 | OMe | OMe | H | —C(=O)— | —CH₂— | (1) | —C(Me)=N— | 0 |
| 9 | OMe | OMe | H | —C(=O)— | —CH(Me)— | (1) | —C(Me)=N— | 0 |
| 10 | —O—CH₂—O— | | H | —CH(OH)— | —CH₂— | (1) | —C(Me)=N— | 0 |
| 11 | OMe | OMe | H | —CH(OH)— | —CH₂— | (1) | —C(Me)=N— | 0 |
| 12 | OMe | OMe | H | —CH(OH)— | —CH(Me)— | (1) | —C(Me)=N— | 0 |
| 13 | —O—CH₂—O— | | H | —C(=O)— | —CH₂— | (1) | —C(NH)=N—CN | 1 |
| 14 | OMe | OMe | H | —C(=O)— | —CH₂— | (1) | —C(NH)=N—CN | 1 |
| 15 | OMe | OMe | H | —C(=O)— | —CH(Me)— | (1) | —C(NH)=N—CN | 1 |

TABLE 2-continued

Structure of compound

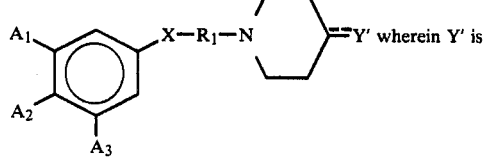
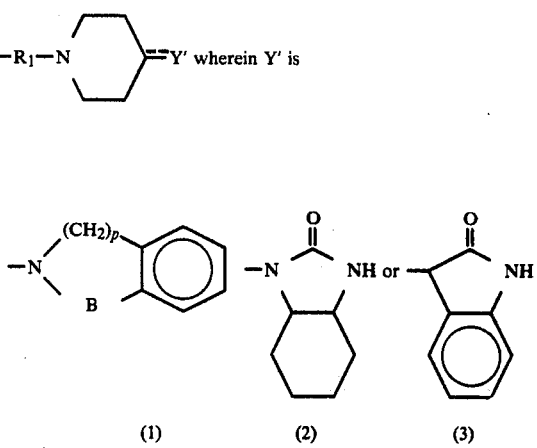

| | (1) | (2) | (3) |

| Compound No. | A₁ | A₂ | A₃ | X | R₁ | Y' | B | p |
|---|---|---|---|---|---|---|---|---|
| 16 | OMe | OMe | OMe | $-\overset{\text{O}}{\underset{\|}{C}}-$ | —CH₂— | (1) | $-\overset{\text{N—CN}}{\underset{\|}{C}}-\text{NH}-$ | 1 |
| 17 | OMe | OMe | OMe | $-\overset{\text{O}}{\underset{\|}{C}}-$ | —CH(Me)— | (1) | $-\overset{\text{N—CN}}{\underset{\|}{C}}-\text{NH}-$ | 1 |
| 18 | O–CH₂–O | | H | $-\overset{\text{O}}{\underset{\|}{C}}-$ | —CH₂— | (1) | $-\overset{\text{N—CN}}{\underset{\|}{C}}-\text{NH}-$ | 0 |
| 19 | OMe | OMe | H | $-\overset{\text{O}}{\underset{\|}{C}}-$ | —CH₂— | (1) | $-\overset{\text{N—CN}}{\underset{\|}{C}}-\text{NH}-$ | 0 |
| 20 | O–CH₂–O | | H | —CH(OH)— | —CH₂— | (1) | $-\overset{\text{N—CN}}{\underset{\|}{C}}-\text{NH}-$ | 1 |
| 21 | OMe | OMe | H | —CH(OH)— | —CH₂— | (1) | $-\overset{\text{N—CN}}{\underset{\|}{C}}-\text{NH}-$ | 1 |
| 22 | OMe | OMe | H | —CH(OH)— | —CH(Me)— | (1) | $-\overset{\text{N—CN}}{\underset{\|}{C}}-\text{NH}-$ | 1 |
| 23 | OMe | OMe | OMe | —CH(OH)— | —CH₂— | (1) | $-\overset{\text{N—CN}}{\underset{\|}{C}}-\text{NH}-$ | 1 |
| 24 | OMe | OMe | OMe | —CH(OH)— | —CH(Me)— | (1) | $-\overset{\text{N—CN}}{\underset{\|}{C}}-\text{NH}-$ | 1 |
| 25 | O–CH₂–O | | H | —CH(OH)— | —CH₂— | (1) | $-\overset{\text{N—CN}}{\underset{\|}{C}}-\text{NH}-$ | 0 |
| 26 | OMe | OMe | H | —CH(OH)— | —CH₂— | (1) | $-\overset{\text{N—CN}}{\underset{\|}{C}}-\text{NH}-$ | 0 |
| 27 | O–CH₂–O | | H | $-\overset{\text{O}}{\underset{\|}{C}}-$ | —CH₂— | (3) single bond | — | — |

TABLE 2-continued

Structure of compound

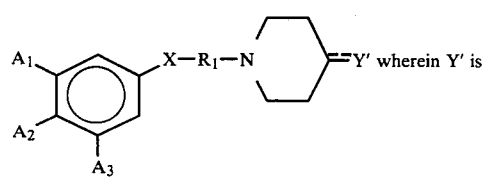Y' wherein Y' is

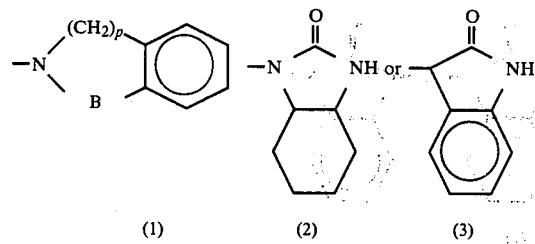

| Compound No. | A₁ | A₂ | A₃ | X | R₁ | Y' | B | p |
|---|---|---|---|---|---|---|---|---|
| 28 | OMe | OMe | H | —C(=O)— | —CH₂— | (3) single bond | — | — |
| 29 | OMe | OMe | H | —C(=O)— | —CH(Me)— | (3) single bond | — | — |
| 30 | —O—CH₂—O— | | H | —C(=O)— | —CH₂— | (3) double bond | — | — |
| 31 | OMe | OMe | H | —C(=O)— | —CH₂— | (3) double bond | — | — |
| 32 | —O—CH₂—O— | | H | —CH(OH)— | —CH₂— | (3) single bond | — | — |
| 33 | OMe | OMe | H | —CH(OH)— | —CH₂— | (3) single bond | — | — |
| 34 | OMe | OMe | H | —CH(OH)— | —CH(Me)— | (3) single bond | — | — |
| 35 | —O—CH₂—O— | | H | —CH(OH)— | —CH₂— | (3) double bond | — | — |
| 36 | OMe | OMe | H | —CH(OH)— | —CH₂— | (3) double bond | — | — |
| 37 | OMe | OMe | H | —C(=O)— | —CH₂— | (2) | — | — |
| 38 | OMe | OMe | H | —C(=O)— | —CH(Me)— | (2) | — | — |
| 39 | OMe | OMe | OMe | —C(=O)— | —CH(Me)— | (2) | — | — |

TABLE 2-continued

Structure of compound $$A_1, A_2, A_3 \text{-phenyl-} X-R_1-N\text{-piperidine}=Y' \text{ wherein Y' is}$$

(1) $-N(CH_2)_p\text{-phenyl-B}$ (2) cyclohexyl-N-C(=O)-NH (3) phenyl-C(=O)-NH

| Compound No. | A₁ | A₂ | A₃ | X | R₁ | Y' | B | p |
|---|---|---|---|---|---|---|---|---|
| 40 | OMe | OMe | OMe | —C(=O)— | —CH₂— | (2) | — | — |
| 41 | OMe | OMe | H | —CH(OH)— | —CH₂— | (2) | — | — |
| 42 | OMe | OMe | H | —CH(OH)— | —CH(Me)— | (2) | — | — |
| 43 | OMe | OMe | OMe | —CH(OH)— | —CH(Me)— | (2) | — | — |
| 44 | OMe | OMe | OMe | —CH(OH)— | —CH₂— | (2) | — | — |

TABLE 3

Properties (Melting point, IR, NMR and Elementary analysis)

(1) The term "form" means that state of a compound subjected to the determination of properties.
Blank: free base (2) The values in the column of infrared absorption spectrum (IR) show characteristic maximum absorption of the compounds measured in KBr tablet, except of Compound Nos. 9 and 28 where the measurement was conducted by using chloroform.

(3) The values in the table of nuclear magnetic resonance spectrum (NMR) and δ values based on TMS in CDCl₃ (Compound Nos. 3–9, 13–19, 21, 23, 24, 26, 29, 36, 37, 40, 41 and 43, d₆-dimethylsulfoxide (d₆-DMSO) (Compound Nos. 1, 2, 10–12, 20, 27, 28, 30–35, 38, 39, 42 and 44), d₆-DMSO+CD₃OD (Compound No. 22) or CDCl₃+CD₃OD (Compound No. 25)

(4) Elementary analysis
A: Calculated
F: Found

TABLE 3-1

| Compound No. | Form | m.p. (°C.) | IR (cm⁻¹) |
|---|---|---|---|
| 1 | | 144.5–146.0 | 1675, 1455, 1440, 1261, 1040 |
| 2 | monofumarate | 184–186 | 1685, 1278, 1158 |
| 3 | | 174.5–177 | 1665, 1260, 1164, 1125 |
| 4 | | 148–149 | 1493, 1255, 1245, 1040 |
| 5 | | 173–174 | 3370, 1265, 1242, 1150 |
| 6 | | 222–224 | 3400, 1504, 1255, 1140–1138 |
| 7 | | 174–177 | 1691, 1255 |
| 8 | | 153–155 | 1673, 1255 |
| 9 | | oil | 1667, 1256 |
| 10 | difumarate | 167–169 | 1690, 1235 |
| 11 | difumarate | 214–215.2 | 1695, 1235 |
| 12 | difumarate | 179–181 | 1685, 1255 |
| 13 | | 200–202 | 2300, 1678, 1623, 1588 |
| 14 | | 202–204 | 2320, 1685, 1628, 1590 |
| 15 | | 195–198 | 2300, 1660, 1628, 1588 |
| 16 | | 185–187 | 2300, 1688–1678, 1624, 1588 |
| 17 | | 193–195 | 2300, 1670, |

TABLE 3-1-continued

| Compound No. | Form | m.p. (°C.) | IR (cm⁻¹) |
|---|---|---|---|
| | | | 1624, 1585 |
| 18 | | 196–198 | 2300, 1674, 1625, 1601 |
| 19 | | 137–139 | 2300, 1680, 1626, 1601 |
| 20 | | 239–241 | 2300, 1630, 1590 |
| 21 | | 249–251 | 2300, 1630, 1589 |
| 22 | | 247–249 | 2301, 1628, 1590 |
| 23 | | 218–220 | 2300, 1628, 1589 |
| 24 | | 252–254 | 2301, 1628, 1589 |
| 25 | | 232–233.5 | 2300, 1629, 1601 |
| 26 | | 218–219 | 2300, 1628, 1601 |
| 27 | | 158–165 | 1695–1692 1673, 1243 |
| 28 | | oil | 1695 |
| 29 | | 174–176 | 1690, 1660–1650 1264 |
| 30 | | 167.5–171 | 1698, 1680, 1255 |
| 31 | | 145–146 | 1690, 1670, 1270 |
| 32 | | 177–178 | 1700 |
| 33 | succinate | 166–167 | 1703 |
| 34 | fumarate | 148–152 | 1690, 1250 |
| 35 | | 176–178 | 1692, 1245 |
| 36 | | 98–99 | 1700, 1690, 1473, 1240 |
| 37 | | 179–181 | 1682 |
| 38 | fumarate | 194–196.5 | 1680 |
| 39 | fumarate | 197–199 | 1680 |
| 40 | | 183–187 | 1682 |
| 41 | | 171–172 | 1689–1680 |
| 42 | fumarate | 208.5–209.5 | 1700–1675 |
| 43 | | 123–126 | 1700–1680 |
| 44 | fumarate | 153–155 | 1685–1675 |

TABLE 3-2

| Compound No. | Form | NMR (ppm) |
|---|---|---|
| 1 | | 1.5–3.4, 3.33, 3.6–4.0, 4.0–4.4, 4.6–5.1, 6.13, 6.8–8.2 |
| 2 | monofumarate | 1.5–3.5, 3.85, 4.08, 4.6–5.2, 6.9–8.2 |
| 3 | | 1.33, 1.9–3.5, 3.95, 4.0–5.0, 6.8–8.2 |
| 4 | | 1.6–4.0, 4.4–5.0, 5.92, 6.6–8.3 |
| 5 | | 2.0–4.0, 3.88, 3.95, 4.4–5.0, 6.65–8.3 |
| 6 | | 0.8, 2.0–3.4, 3.85, 4.25, 4.4–5.2, 6.68–8.3 |
| 7 | | 1.6–3.4, 2.6, 3.4–4.6, 3.8, 6.02, 6.7–7.9 |
| 8 | | 1.65–3.4, 2.63, 3.6–4.6, 3.88, 3.98, 6.7–7.9 |
| 9 | | 1.33, 1.4–3.4, 2.60, 3.6–4.6, 3.97, 6.70–8.0 |
| 10 | difumarate | 1.6–4.0, 2.63, 4.2–5.2, 6.03, 6.7–8.05 |
| 11 | difumarate | 1.7–4.0, 2.63, 3.75, 3.80, 4.2–5.2, 6.8–8.1 |
| 12 | difumarate | 0.81, 1.6–4.0, 2.6, 3.76, 3.80, 4.2–4.7, 6.8–8.1 |
| 13 | | 1.4–3.4, 3.76, 4.2–4.9, 4.4, 6.05, 6.7–7.8, 8.65 |
| 14 | | 1.4–3.4, 3.79, 3.95, 4.2–4.8, 4.4, 6.7–7.8, 8.74 |
| 15 | | 1.25, 1.4–3.4, 3.94, 4.0–4.6, 4.34, 6.8–7.9, 8.4 |
| 16 | | 1.3–3.4, 3.78, 3.88, 4.2–4.8, 4.36, 6.8–7.2, 8.95 |
| 17 | | 1.3, 1.4–3.4, 3.95, 4.0–4.6, 4.38, 6.8–7.6, 8.62 |
| 18 | | 1.4–4.2, 4.3–4.9, 6.2, 6.9–8.0 |
| 19 | | 1.5–4.1, 3.9, 4.0, 4.3–4.9, 6.8–8.0 |
| 20 | | 1.3–3.4, 4.0–5.0, 4.39, 5.85, 6.6–7.4, 9.92 |
| 21 | | 1.4–4.0, 3.85, 3.90, 6.6–7.4, 8.90 |
| 22 | | 0.75, 1.4–3.4, 3.80, 3.90, 4.1–5.0, 4.1–5.0, 6.6–7.4 |
| 23 | | 1.4–4.0, 3.8, 3.85, 4.1–4.8, 4.35, 6.59, 6.8–7.33, 8.96 |
| 24 | | 0.8, 1.4–4.0, 3.8, 3.85, 4.0–4.8, 4.41, 6.6, 6.8–7.33, 9.00 |
| 25 | | 1.7–5.0, 6.0, 6.8–7.8 |
| 26 | | 1.6–5.0, 3.88, 3.91, 6.8–7.8 |
| 27 | | 1.0–3.5, 3.62, 6.1, 6.7–7.8, 10.26 |
| 28 | | 1.0–3.5, 3.65, 3.8, 3.85, 6.7–7.8, 10.26 |
| 29 | | 1.0–3.5, 1.23, 3.8–4.2, 6.7–7.2, 7.6–8.0, 9.1 |
| 30 | | 2.3–3.6, 3.8, 6.1, 6.7–7.8, 10.32 |
| 31 | | 2.4–3.6, 3.3, 3.82, 6.7–7.85, 10.3 |
| 32 | | 1.0–3.4, 4.4–4.8, 5.92, 6.6–7.4, 10.21 |
| 33 | succinate | 1.2–3.5, 3.75, 4.5–4.95, 6.67–7.5, 10.25 |
| 34 | fumarate | 1.0, 1.2–3.5, 3.75, 4.1–4.4, 6.6–7.4, 10.3 |
| 35 | | 2.3–3.2, 3.2–3.6, 4.4–5.15, 5.95, 6.6–7.7, 10.35 |
| 36 | | 2.3–3.4, 3.4–4.0, 3.93, 4.4–5.0, 6.68–7.75, 8.65 |
| 37 | | 1.0–4.0, 3.77, 3.95, 4.95, 6.77–7.8 |
| 38 | fumarate | 1.0–4.0, 1.12, 3.8, 6.9–7.88 |
| 39 | fumarate | 1.0–4.0, 1.18, 3.8, 3.85, 7.5 |
| 40 | | 1.0–4.0, 3.8, 3.9, 7.42 |
| 41 | | 1.0–4.0, 3.85, 3.90, 4.4–5.0, 6.65–7.07 |
| 42 | fumarate | 0.73, 1.0–3.3, 3.75, 4.3, 6.7–7.08 |
| 43 | | 0.75, 1.0–3.2, 3.82, 3.85, 4.12, 4.88, 6.59 |
| 44 | fumarate | 1.0–4.0, 3.9, 6.5–7.0 |

TABLE 3-3

| Compound No. | Rational formula | A: Calculated, F: Found | Elementary analysis (%) | | |
|---|---|---|---|---|---|
| | | | C | H | N |
| 1 | C₂₀H₂₀N₄O₃ | A | 65.92 | 5.53 | 15.38 |
| | | F | 65.86 | 5.52 | 15.68 |
| 4 | C₂₀H₂₂N₄O₃ | A | 65.55 | 6.05 | 15.29 |
| | | F | 65.32 | 6.04 | 15.44 |
| 8 | C₂₃H₂₇N₃O₃ | A | 70.20 | 6.92 | 10.68 |
| | | F | 70.22 | 6.99 | 10.56 |
| 11 | C₂₃H₂₉N₃O₃·C₈H₈O₈ | A | 59.32 | 5.94 | 6.69 |
| | | F | 59.11 | 5.94 | 6.66 |
| 13 | C₂₃H₂₃N₅O₃ | A | 66.17 | 5.55 | 16.78 |
| | | F | 66.09 | 5.43 | 16.63 |
| 17 | C₂₆H₃₁N₅O₄ | A | 65.39 | 6.54 | 14.67 |
| | | F | 65.31 | 6.58 | 14.42 |
| 18 | C₂₂H₂₁N₅O₃ | A | 65.49 | 5.25 | 17.36 |
| | | F | 65.22 | 5.34 | 17.35 |
| 20 | C₂₃H₂₅N₅O₃ | A | 65.85 | 6.01 | 16.70 |
| | | F | 65.77 | 6.02 | 16.61 |
| 25 | C₂₂H₂₃N₅O₃ | A | 65.17 | 5.72 | 17.28 |
| | | F | 65.24 | 5.62 | 17.13 |
| 27 | C₂₂H₂₂N₂O₄ | A | 69.82 | 5.86 | 7.40 |
| | | F | 69.73 | 5.77 | 7.40 |
| 29 | C₂₄H₂₈N₂O₄ | A | 70.56 | 6.91 | 6.86 |
| | | F | 70.33 | 7.12 | 6.85 |

TABLE 3-3-continued

| Compound No. | Rational formula | A: Calculated, F: Found | Elementary analysis (%) | | |
|---|---|---|---|---|---|
| | | | C | H | N |
| 30 | $C_{22}H_{20}N_2O_4$ | A | 70.20 | 5.36 | 7.44 |
| | | F | 69.96 | 5.29 | 7.33 |
| 32 | $C_{22}H_{24}N_2O_4$ | A | 69.45 | 6.36 | 7.36 |
| | | F | 69.30 | 6.37 | 7.07 |
| 34 | $C_{28}H_{34}N_2O_8$ | A | 63.86 | 6.51 | 5.32 |
| | | F | 63.77 | 6.63 | 5.30 |
| 35 | $C_{22}H_{22}N_2O_4$ | A | 69.82 | 5.86 | 7.40 |
| | | F | 69.67 | 5.84 | 7.33 |
| 37 | $C_{22}H_{31}N_3O_4$ | A | 65.81 | 7.78 | 10.47 |
| | | F | 65.75 | 7.91 | 10.20 |
| 41 | $C_{22}H_{33}N_3O_4$ | A | 65.48 | 8.24 | 10.41 |
| | | F | 65.31 | 8.43 | 10.41 |

Hypotensive activity and acute toxicity of Compound [I] are illustrated below as experiments.

Experiment 1

This experiment is conducted according to the method described in "Spontaneously Hypertensive Rats (SHR) Guidelines for Breeding, Care and Use" (published by SHR Conference) (1976) p. 11.

Five spontaneously hypertensive rats (15 weeks old, 180 mmHg of more in blood pressure) are used as one group. Each of the test compounds is added to 0.3% (w/v) CMC aqueous solution in a concentration of 3 mg/ml. Each of the mixtures is orally administered to the rats in a dose of 1 ml/100 g. Changes in blood pressure are measured according to the method of tail artery plethysmography (see the literature cited above). The maximum reduction (mmHg) in blood pressure after the administration on the basis of the pressure immediately before the administration is shown in Table 4.

TABLE 4

| Compound No. | Maximum reduction in blood pressure (mm Hg) |
|---|---|
| 1 | 15 |
| 2 | 19 |
| 3 | 22 |
| 4 | 23 |
| 5 | 28 |
| 6 | 30 |
| 7 | 21*1 |
| 8 | 11*1 |
| 9 | 3 |
| 10 | 5*1 |
| 11 | 17 |
| 12 | 13 |
| 13 | 14 |
| 14 | 22 |
| 15 | 38 |
| 16 | 18 |
| 17 | 8 |
| 18 | 25 |
| 19 | 31 |
| 20 | 38 |
| 21 | 32 |
| 22 | 37 |
| 23 | 40 |
| 24 | 33 |
| 25 | 19 |
| 26 | 23 |
| 27 | 6 |
| 28 | 11 |
| 29 | 13 |
| 30 | 17.5*2 |
| 31 | 30 |
| 32 | 7 |
| 33 | 11 |
| 34 | 25 |
| 35 | 5 |
| 36 | 5 |
| 37 | 38 |
| 38 | 17 |
| 39 | 33 |
| 40 | 30 |
| 41 | 20 |
| 42 | 22 |
| 43 | 27 |
| 44 | 28 |

*1 50 mg/kg administration
*2 100 mg/kg administration

Experiment 2

The compound of Compound No. 23 is used as a test compound. Three male dd-strain mice (weight 20±1 g) are used for the test compound.

The compound is added to aqueous physiological sodium chloride, and the mixture is orally (P.O.) administered to the mice in a dose of 300 mg/kg. After the observation for 7 days, the numbers of deaths are counted. The result is that no death is observed.

Now, the process for preparing Compound [I] is described below.

Compound [I] may be prepared by reacting a compound represented by the formula [II]:

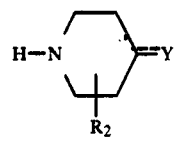

(wherein $R_2$ and Y have the same definitions as defined in Formula [I] or Compound [II] wherein $R_3$ of the Y group is protected, with a compound represented by the formula [III]

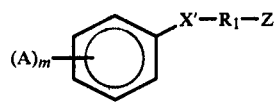

wherein A, m and $R_1$ have the same definitions as defined in Formula [I]; X' is oxygen, sulfur, carbonyl or methylene; and Z is halogen or an eliminable group, or Compound [III] wherein A is protected, and further if necessary, by reducing the resulting product and if necessary, by eliminating the protective group therefrom.

In the definition of Z, halogen includes chlorine, bromine and iodine; and the eliminable group includes alkylsulfonyloxy (for example, methanesulfonyloxy), arylsulfonyloxy (for example, benzenesulfonyloxy and p-toluenesulfonyloxy), etc.

The reaction of Compound [II] or the protected one with Compound [III] or the protected one is carried out in an inert solvent. Ketone (e.g. acetone), halogenated hydrocarbon (e.g. chloroform and methylene chloride), amide (e.g. dimethylformamide), sulfoxide (e.g. dimethylsulfoxide), substituted or unsubstituted aromatic hydrocarbon (e.g. benzene, toluene and chlorobenzene), lower alcohol (e.g. methanol, ethanol and isopropanol), etc. may be used alone or in combination as an inert solvent. The reaction is carried out at 0°-15° C., preferably at a temperature between room temperature and the boiling point of the solvent depending on the reactivity of the group Z which is exchangeable. The reaction usually proceeds very smoothly in the presence of a base such as lower alcoholate (e.g. sodium methylate and sodium ethylate), alkali hydroxide (e.g. sodium hydroxide), alkali carbonate (e.g. sodium carbonate and potassium carbonate), tertiary amine (e.g. triethylamine and pyridine), etc. The amount of the base is usually 1.0 to 1.2 times the equivalent amount based on Compound [II]. When an acid addition salt of Compound [II] such as hydrochloride is used, it goes without saying that the base supplementary enough to neutralize the acid is added thereto. Use of reaction-promoting agents such as potassium iodide is effective for smooth proceeding of the reaction.

When either $R_3$ or A, or both is(are) hydroxy, amino or lower alkylamino, these groups are protected in a conventional manner prior to the above reaction. After completion of the reaction, the protective group is eliminated in a conventional manner to obtain the desired product.

When X′ is carbonyl, the resulting product is reduced to obtain Compound [I] wherein X is hydroxymethylene. The reaction may be carried out by reacting Compound [I] wherein X is carbonyl with a complex metal hydride such as sodium borohydride in a lower alcohol such as methanol, ethanol and isopropanol at −10° to 100° C., preferably at a temperature between 0° C. and the boiling point of the used solvent. Alternatively, the reaction may be carried out by subjecting Compound [I] wherein X is carbonyl to catalytic reduction using hydrogenating catalyst such as palladium carbon, Raney nickel, platinum black, platinum carbon and platinum oxide in lower alcohol such as methanol and ethanol, lower aliphatic acid such as acetic acid, water or a mixed solvent thereof. These reactions may be carried out either in an open vessel or in a closed vessel under pressure. When the carbon atom of $R_1$ adjacent to X is an asymmetrical carbon in the above reduction, Compound [I] is stereo-selectively obtained according to the reduction method. That is, Compound [I] in threo form is obtained when a complete metal hydride is used and Compound [I] in erythro form is obtained according to catalytic reduction in an acidic condition. The acidic condition is brought with inorganic acids such as hydrochloric acid or organic acids such as acetic acid, propionic acid and succinic acid.

Compound [II] used as a starting compound of Compound [I] is also new compound. Compound [II] is classified as described in Table 6 for convenience.

TABLE 6

| Y | P | B | Compound No. | Formula |
|---|---|---|---|---|
| (1) | 0 | —N=N— | II-1 | |
| (1) | 0 | —C=N—<br>\|<br>Me | II-2 | |
| (1) | 0 | —C—NH—<br>‖<br>N—CN | II-3 | |
| (1) | 1 | —C—NH—<br>‖<br>N—CN | II-4 | |
| (2) | — | — | II-5 | |

TABLE 6-continued

| Y | P | B | Compound No. | Formula |
|---|---|---|---|---|
| (3) | — | — | II-6 | 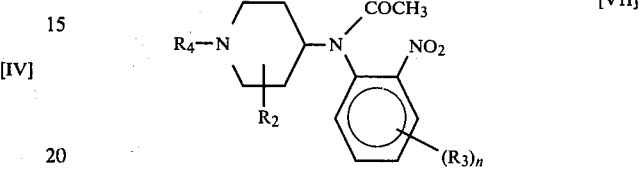 |

Compound [II-1] is produced as shown below. First, an o-phenylenediamine derivative represented by the formula [IV]:

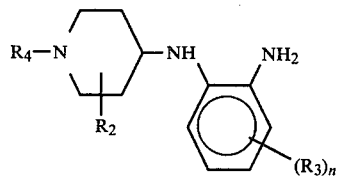

(wherein $R_2$, $R_3$ and n have the same definitions as heretofore defined and $R_4$ is an amino-protecting group) is reacted with a nitrite such as sodium nitrite under an acidic condition to prepare a compound represented by the formula [V]:

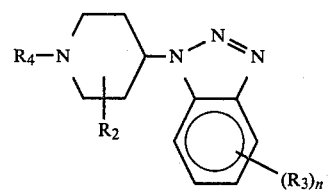

(wherein $R_2$, $R_3$, $R_4$ and n have the same definitions as heretofore defined).

It is proper to use sodium nitrite in an amount of 1 to 1.1 mols per mol of Compound [IV].

This reaction can be effectively carried out in an appropriate solvent such as water and acetic acid in combination thereof or alone at $-10°$ C. to $10°$ C.

Examples of the substituent $R_4$ in Compound [IV] are acyl (e.g. acetyl and benzoyl), alkyloxycarbonyl (e.g. tert.-butoxycarbonyl and ethoxycarbonyl), benzyl, tosyl and mesyl.

Finally, Compound [V] is converted to Compound [II-1] by being subjected to the usual reaction for eliminating the amino-protecting group.

Compound [II-2] is produced as shown below. First, a piperidine derivative represented by the formula [VI]:

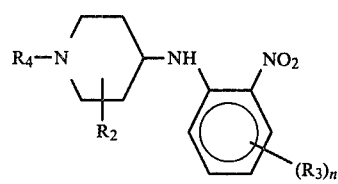

(wherein $R_2$, $R_3$, $R_4$ and n have the same definitions as defined above) is acetylated to prepare an acetyl derivative represented by the formula [VII]:

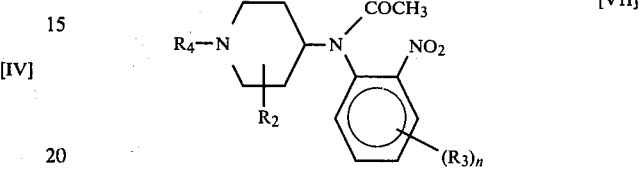

(wherein $R_2$, $R_3$, $R_4$ and n have the same definitions as defined above). The acetylation can be effectively performed by heating Compound [VI] and an acetyl halide such as acetyl chloride, acetyl bromide and acetyl iodide in an inert solvent such as dioxane and dimethylformamide. It is proper to use the acetyl halide in an amount of 3 to 10 equivalent weights of Compound [VI]. The proper reaction temperature is 50° C. to 120° C.

Then, Compound [VII] is reduced for conversion of the nitro group to amino group and thereafter the reaction mixture is acidified or Compound [VII] is reduced under an acidic condition whereby a benzimidazole derivative represented by the formula [VIII]:

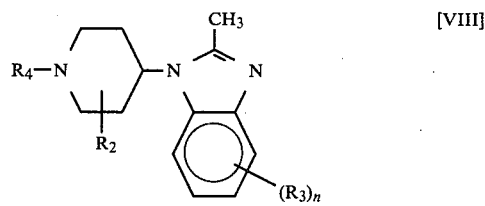

(wherein $R_2$, $R_3$, $R_4$ and n have the same definitions as defined above) is obtained.

The conversion of the nitro group into the amino group can be accomplished by the methods generally adopted for the purpose, for example, catalytic reduction using palladium carbon or Raney nickel as a catalyst, a method using tin or a tin compound under an acidic condition and a method using a complex metal hydride such as lithium aluminum hydride. From the compound which has resulted from conversion into amino group, Compound [VIII] can be readily derived by directly acidifying the reaction mixture. When the reduction is carried out under an acidic condition as in the use of a tin compound, reduction of the nitro group and the ring-closing to benzimidazole can be simultaneously accomplished. The method to be adopted for reduction of the nitro group may be suitably selected depending on the kind of the protective group $R_4$ in the formula [VII]. When a protective group such as the benzyl group which can be removed by hydrogenation is selected as the substituent $R_4$, reduction of the nitro group and removal of the protective group, or reduction of the nitro group, the ring-closing into a benzimidazole derivative and removal of the protective group can be simultaneously effected.

Of the aforementioned various methods available for the reduction, that which involves use of palladium carbon or a tin compound will be explained in detail below. The reduction using palladium carbon is carried out in an inert solvent under continuous introduction of hydrogen usually at room temperature to 50° C. for 2 to 10 hours. Examples of the solvent include lower alcohols such as methanol, ethanol and isopropanol, lower fatty acids such as acetic acid, water, dioxane, etc. and mixtures thereof.

The reduction using a tin compound is carried out in an inert solvent in the presence of a mineral acid such as hydrochloric acid or a lower fatty acid such as acetic acid usually at room temperature to 80° C. for 2 to 10 hours. Examples of the solvent include water, dioxane, lower alcohols, etc. and mixtures thereof.

Finally, Compound [VIII] is converted into Compound [II-2] by being subjected to the usual reaction for eliminating an amino-protecting group.

Compound [II-3] is produced as shown below. First, Compound [IV] is reacted with dimethyl-N-cyanodithioimino-carbonate

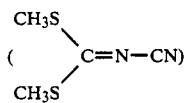

in an inert solvent to prepare a compound represented by the formula [IX]:

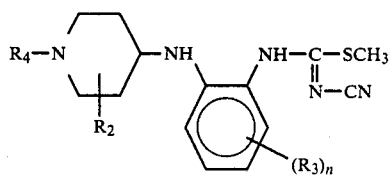

(wherein $R_2$, $R_3$, $R_4$ and n have the same definitions as defined above).

It is proper to use dimethyl-N-cyanodithioimino-carbonate in an amount of about 1 mol per mol of Compound [IV]. Examples of the inert solvents include alcohols such as methanol, ethanol and isopropanol, dioxane, dimethoxy-methane, dimethoxy-ethane, dimethylsulfoxide and dimethylformamide. The reaction is carried out at room temperature to 150° C. and is usually completed in 2 to 24 hours.

Then, Compound [IX] is subjected to a ring-closing reaction in an inert solvent in the presence of a metal ion to prepare a compound represented by the formula [X]:

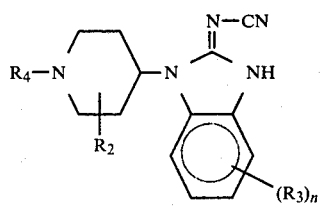

(wherein $R_2$, $R_3$, $R_4$ and n have the same definitions as defined above).

Examples of suitable metal ions include $Hg^{2+}$ and $Ag^+$. Mercuric acetate, mercuric chloride, etc. are usable as sources of $Hg^{2+}$ and silver acetate, silver trifluoroacetate, silver fluoroborate, silver methanesulfonate, etc., as sources of $Ag^+$. The reaction temperature is desirably from 0° C. to 80° C. The proper concentration of metal ion is from 1 to 1.2 mols per mol of the compound [X]. Generally, the reaction is completed in 15 minutes to 2 hours. Examples of the reaction solvents include alcohols (e.g. methanol, ethanol and isopropanol), chloroform, dichloromethane, dioxane, etc.

Finally, Compound [X] is converted to Compound [II-3] by being subjected to the usual reaction for eliminating the amino-protecting group.

Compound [II-4] is produced as shown below. First, an 4-amino-piperidine derivative represented by the formula [XI]:

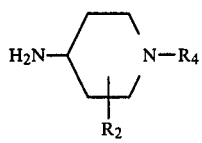

(wherein $R_2$ and $R_4$ have the same definitions as defined above) is reacted with a compound represented by the formula [XII]:

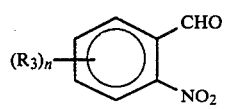

(wherein $R_3$ and n have the same definitions as defined above) to prepare a compound represented by the formula [XIII]:

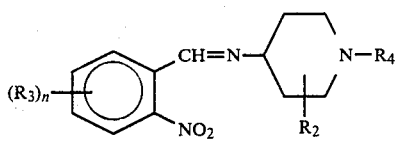

(wherein $R_2$, $R_3$, $R_4$ and n have the same definitions as defined above).

The reaction can be carried out either without any solvent or in a lower alkanol (e.g. methanol, ethanol and propanol), an aromatic hydrocarbon (e.g. benzene, toluene and xylene), a halogenated hydrocarbon (e.g. methylene chloride and chloroform) or a mixture thereof. The reaction in an alkanol has the advantage that the conversion to a compound represented by the formula [XIV] below can be carried out without isolation of Compound [XIII] from the reaction solution. As regards the amounts of the reactants to be used, it is proper to use Compound [XII] in an amount of 1.0 to 1.2 equivalent weights, preferably 1.0 equivalent weight, of Compound [XI]. Although the reaction proceeds at room temperature in a short time, it may be carried out at an elevated temperature, if necessary.

Then, Compound [XIII] is reduced with a complex metal hydride (e.g. sodium borohydride and sodium cyanoborohydride) in a lower alkanol (e.g. methanol, ethanol and isopropanol) to prepare a 4-substituted piperidine derivative represented by the formula [XIV]:

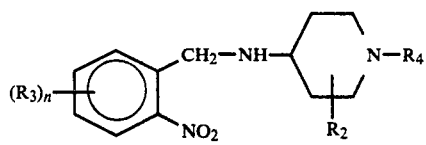

(wherein $R_2$, $R_3$, $R_4$ and n have the same definitions as defined above).

This reaction is advantageously carried out at −10° C. to 100° C., preferably 0° C. to room temperature.

Then, Compound [XIV] is further reduced to prepare a compound represented by the formula [XV]:

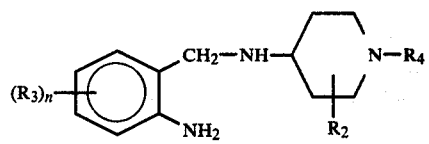

(wherein $R_2$, $R_3$, $R_4$ and n have the same definitions as defined above).

This reaction can be performed by the methods generally adopted for the purpose of reducing a nitro group into an amino group, for example, the method involving combined use of a metal such as Sn, Fe or Zn and a mineral acid such as hydrochloric acid and sulfuric acid or an organic acid such as acetic acid, the method resorting to use of a sulfide or hydrazine and the catalytic reduction in the presence of a catalyst such as palladium carbon. When the reduction is performed by the catalytic method, the reaction is effected by causing the Compound [XIV] to absorb an equivalent weight of hydrogen in water, a lower alkanol such as methanol and ethanol, or a mixture thereof. The reaction is preferably carried out 20° C. to 60° C., especially around room temperature.

Compound [XV] is reacted with dimethyl-N-cyanodithioimino-carbonate to prepare a compound represented by the formula [XVI]:

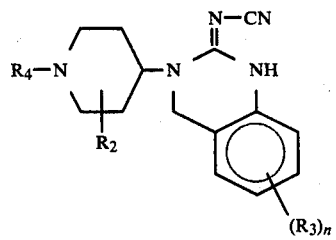

(wherein $R_2$, $R_3$, $R_4$ and n have the same definitions as defined above).

This reaction can be performed similarly to that which is involved in the preparation of Compound [IX] from Compound [IV]. Then, Compound [XVI] is converted into Compound [II-4] by eliminating the group $R_4$ by the usual methods.

Compound [II-5] is produced as shown below. First, Compound [XI] is reacted with 1-nitrocyclohexene or a derivative thereof represented by the formula [XVII]:

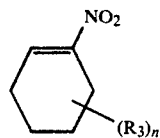

(wherein $R_3$ and n have the same definitions as defined above) to prepare a compound represented by the formula [XVIII]:

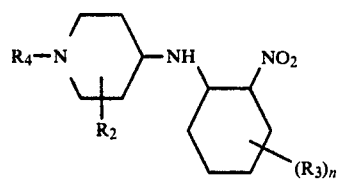

(wherein $R_2$, $R_3$, $R_4$ and n have the same definitions as defined above).

This reaction is performed in an inert organic solvent such as benzene, toluene, chloroform, dichloromethane, ether, tetrahydrofuran, dimethylformamide and dimethylsulfoxide at a temperature of 0° C. to 100° C., preferably around room temperature for 2 to 24 hours.

Then, a compound represented by the formula [XIX]:

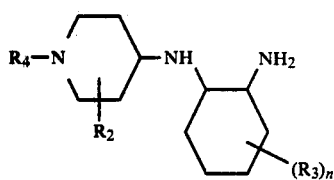

(wherein $R_2$, $R_3$, $R_4$ and n have the same definitions as defined above) is produced by reducing Compound [XVIII]. This reduction can be performed similarly to that in the preparation of Compound [XV] from Compound [XIV].

Compound [XIX] is then reacted with a carbonic acid derivative such as phosgene, trichloromethylchloroformate, alkyl chlorocarbonate, 1,1'-carbonyldiimidazole and urea to prepare a compound represented by the formula [XX]:

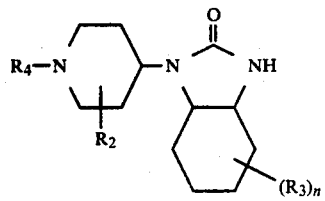

(wherein $R_2$, $R_3$, $R_4$ and n have the same definitions as defined above).

All of the above reactions can be carried out according to conventional methods and the reaction wherein 1,1'-carbonyldiimidazole is used is particularly described hereinafter. The reaction is carried out in an aprotic polar solvent such as halogenated hydrocarbon (e.g. methylene chloride and chloroform), ether (e.g. ethyl ether, tetrahydrofuran and dioxane), acetonitrile, dimethylformamide and dimethylsulfoxide, in combination thereof or alone, preferably with stirring. Preferably, the amount of 1,1′-carbonyldiimidazole is 1.2 to 2.0 times the equivalent amount based on Compound [XIX]. The reaction is carried out at a temperature of from room temperature to the boiling point of the used solvent. The reaction is usually completed in 1 to 6 hours.

Finally, Compound [XX] is converted to Compound [II-5] by eliminating the group $R_4$ by the usual methods.

Compound [II-6] is produced as shown below. First, a 4-oxo-piperidine derivative represented by the formula [XXI]:

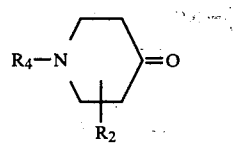

[XXI]

(wherein $R_2$ and $R_4$ have the same definitions as defined above) is reacted with a compound represented by the formula [XXII]:

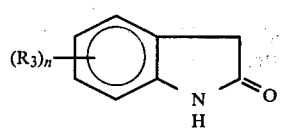

[XXII]

(wherein $R_3$ and n have the same definitions as defined above) to prepare a compound represented by the formula [XXIII]:

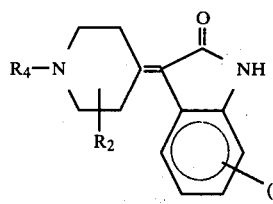

[XXIII]

(wherein $R_2$, $R_3$, $R_4$ and n have the same definitions as defined above).

The reaction can be performed in a lower alkanol (e.g. methanol, ethanol and propanol) in the presence of a base such as ammonia at 0° C. to 100° C. Then, Compound [XXIII] is converted to Compound [II-6] by a method generally adopted for the purpose of removing a protective group from an amino group.

In this case, the choice between the presence and absence of the exo double bond at the 4-position of the piperidine in Compound [II-6] can be freely made by suitably selecting the kind of the protective group $R_4$ and the method for the removal of this group.

Isolation and purification of Compound [I] as well as the above-mentioned intermediates are carried out according to conventional methods in the field of organic synthetic chemistry, for example, concentration, extraction, recrystallization and chromatography. Specifically, since Compound [I] readily crystallizes in general, it can be isolated and purified by distilling off the solvent from the reaction mixture and recrystallizing the residue from a suitable solvent such as ethanol.

A pharmacologically acceptable acid addition salt of Compound [I] may be obtained by reacting Compound [I] with a suitable acid in a suitable solvent such as ethanol.

The pharmaceutical compositions of the present invention are described below.

It is apparent from the foregoing various experimental data that Compound [I] has a hypotensive activity.

In view of the hypotensive activity, the compounds of the present invention may be used in various pharmaceutical forms for administration. Pharmaceutical compositions of the present invention are prepared by uniformly mixing an effective amount of the compound in the form of a base or an acid addition salt as an active ingredient with a pharmaceutically acceptable carrier. According to the pharmaceutical forms suitable for administration, the carrier may take various forms. It is desirable that the pharmaceutical compositions are in single administration form suitable for administration per os or by injection.

In preparation of the composition for oral administration, any useful pharmaceutical carrier may be used. For example, water, glycols, oils, alcohols, etc. may be used to prepare oral liquid preparations such as suspensions and syrups, and excipients, lubricants, binders, disintegrators, etc. may be used to prepare powders, pills, capsules and tablets. Examples of the carriers are glucose and lactose as the excipients starch and sodium alginate as the disintegrators, magnesium stearate, paraffin sulfate and talc as the lubricants, and syrup, ethanol and gelatin as the binders. The active ingredient is orally administered in a dose of 1–100 mg, particularly 10–60 mg, per day for an adult.

The preparation of Compound [I] and the present pharmaceutical compositions are illustrated by the following examples, and the preparation of the intermediates is illustrated by the following reference examples.

EXAMPLE 1:
1-[2-(3,4-Methylenedioxyphenyl)-2-oxo-ethyl]-4-(1H-benzotriazol-1-yl)-piperidine:

In this example, 3.7 g of ω-bromo-3,4-methylenedioxy-acetophenone is added to a solution of 4.0 g of 4-(1H-benzotriazol-1-yl)-piperidine hydrochloride and 3.1 g of triethylamine in 50 ml of methanol and the mixture is stirred overnight at room temperature. The reaction mixture is concentrated and the residue is mixed with 50 ml of ethyl acetate and 50 ml of water to separate an organic layer. The organic layer is washed with water several times, dried and concentrated. The residue is recrystallized from isopropyl alcohol to obtain 3.2 g of the desired product.

Example 2:
1-[2-(3,4-Methylene-dioxyphenyl)-2-hydroxyethyl]-4-(1H-benzotriazol-1-yl)-piperidine:

In this example, 1.75 g of 1-[2-(3,4-methylene-dioxyphenyl)-2-oxo-ethyl]-4-(1-benzotriazol-1-yl)-piperidine obtained in Example 1 is suspended in 30 ml of methanol. To this suspension, 190 mg of sodium borohydride is added at room temperature over a period of 30 minutes. After completion of the addition, the reaction mixture is heated to 40° C. and stirred for one hour. The reaction mixture is concentrated. The residue is mixed with 20 ml of water, stirred and then filtered. The cake is dried to obtain 1.61 g of crude crystals. The crude crystals are recrystallized from ethanol to obtain 1.4 g of the desired product.

Example 3:
1-[2-(3,4-Dimethoxyphenyl)-2-oxo-ethyl]-4-(2-methyl-benzimidazol-3-yl)-piperidine:

A solution of 2.8 g of 4-(2-methyl-benzimidazol-3-yl)-piperidine, 1.32 g of triethylamine and 3.37 g of ω-dimethoxy-acetophenone in 50 ml of methanol is stirred at room temperature for 10 hours. The reaction mixture is concentrated. The residue is mixed with ethyl acetate and water and shaken and then the organic layer is separated. The organic layer is washed with 30 ml of water four times and then dried. The dried organic layer is concentrated to dryness under reduced pressure. The residue is recrystallized from isopropyl alcohol twice to obtain 2.72 g of the desired product.

Example 4:
1-[2-(3,4-Dimethoxyphenyl)-2-hydroxyethyl]-4-(2-methyl-benzimidazol-3-yl)-piperidine difumarate:

In this example, 1.38 g of 1-[2-(3,4-dimethoxyphenyl)-2-oxo-ethyl]-4-(2-methyl-benzimidazol-3-yl)-piperidine obtained in Example 3 is dissolved in 40 ml of methanol. To this solution, 0.13 g of sodium borohydride is added with stirring over a period of 30 minutes. The resultant mixture is further stirred for 2 hours and then concentrated. The residue is mixed with a small amount of water. The mixture is extracted with 20 ml of chloroform three times. The chloroform layer is washed with water and dried. The layer is concentrated to dryness under reduced pressure. The residual oily substance is dissolved in 10 ml of ethanol. The solution is mixed with 0.8 g of fumaric acid and stirred. The crystals deposited are separated by filtration and dried. The crude crystals are recrystallized from methanol to obtain 1.28 g of the desired product.

Example 5:
1-(3,4-Methylenedioxybenzoylmethyl)-4-(2-cyanoimino-3,4-dihydro-1H-quinazolin-3-yl)-piperidine:

In this example, 1.74 g of ω-bromo-3,4-methylene-dioxy-acetophenone is added to a solution of 2.4 g of 4-(2-cyanoimino-3,4-dihydro-1H-quinazolin-3-yl)-piperidine hydrochloride and 2.5 g of triethylamine in 50 ml of methanol. The mixture is stirred overnight at room temperature. The reaction mixture is concentrated. The residue is mixed with 10 ml of water and stirred and the crystals deposited are separated by filtration. The crystals are washed with water and methanol and dried. The crude crystals are recrystallized from methanol to obtain 1.9 g of the desired product.

Example 6:
1-[2-(3,4-Methylene-dioxyphenyl)-2-hydroxyethyl]-4-(2-cyanoimino-3,4-dihydro-1H-quinazolin-3-yl)-piperidine:

In this example, 1.16 g of the product obtained in Example 5 is suspended in 30 ml of ethanol. While the suspension is stirred, 2.0 g of sodium borohydride is added thereto over a period of one hour. After the addition, the resultant mixture is heated to 50° C. and allowed to undergo reaction for 2 hours. The reaction mixture is concentrated to dryness under reduced pressure. The residue is mixed with 10 ml of water and the deposited crystals are separated by filtration. The crystals are washed with water and ethanol and then dried. The crude crystals are recrystallized from chloroform-methanol to obtain 923 mg of the desired product.

Example 7:
1-[2-(3,4,5-Trimethoxyphenyl)-2-oxo-1-methylethyl]-4-(2-cyanoimino-3,4-dihydro-1H-quinazolin-3-yl)-piperidine:

In this example, 2.17 g of ω-bromo-3,4,5-trimethoxy-propiophenone is added to a solution of 2.4 g of 4-(2-cyanoimino-3,4-dihydro-1H-quinazolin-3-yl)-piperidine hydrochloride and 2.5 g of triethylamine in 50 ml of methanol. The mixture is allowed to react at room temperature for 12 hours. The solution is concentrated, the residue is mixed with 15 ml of water and the mixture is stirred. The crystals deposited are separated by filtration. The crystals are washed with water and ethanol and then dried. The crude crystals are recrystallized from methanol to obtain 1.4 g of the desired product.

Example 8:
1-[2-(3,4,5-Trimethoxyphenyl)-2-hydroxy-1-methylethyl]-4-(2-cyanoimino-3,4-dihydro-1H-quinazolin-3-yl)-piperidine:

In this example, 848 mg of the product obtained in Example 7 is dissolved in 30 ml of ethanol. The solution is subjected to reaction in the same conditions as those of Example 6 by using 1 g of sodium borohydride. The reaction mixture is subjected to the same post-treatment as that of Example 6 to obtain crude crystals. The crude crystals are recrystallized from methanol to obtain 554 mg of the desired product.

Example 9:
1-[2-(3,4-Methylenedioxyphenyl)-2-oxo-ethyl]-4-(2-cyanoimino-1H-benzimidazol-1-yl)-piperidine:

In this example, 1.9 g of ω-bromo-3,4-methylenedioxyacetophenone is added to a solution of 2.5 g of 4-(2-cyanoimino-1H-benzimidazol-1-yl)-piperidine hydrochloride and 2.75 g of triethylamine in 20 ml of methanol. The mixture is allowed to react at room temperature for 12 hours. The solution is concentrated and the residue is mixed with 20 ml of water and stirred. The crystals formed therein are separated by filtration, washed with water and ethanol and then dried. The crude crystals are recrystallized from methanol to obtain 1.8 g of the desired product.

Example 10:
1-[2-(3,4-Methylenedioxyphenyl)-2-hydroxyethyl]-4-(2-cyanoimino-1H-benzimidazol-1-yl)-piperidine:

In this example, 600 mg of sodium borohydride is added to a suspension of 715 mg of the product obtained in Example 9 in 30 ml of ethanol at room temperature. After completion of the addition, the reaction mixture is concentrated. The residue is mixed with water, and the crystals deposited are separated by filtration and dried. The crude crystals are recrystallized from methanol to obtain 632 mg of the desired product.

Example 11:
1-(3,4-Methylenedioxybenzoylmethyl)-4-(2-oxyindol-3-yl)-piperidine:

In this example, 4.45 g of ω-bromo-3,4-methylenedioxy-acetophenone is added to a solution of 4.62 g of 4-(2-oxyindol-3-yl)-piperidine hydrochloride and 3.8 g of triethylamine in 100 ml of methanol. The mixture is stirred overnight at room temperature. The reaction mixture is concentrated. The residue is mixed with 50 ml of water, stirred and filtered. The crystals are washed with 20 ml of water and 10 ml of ethanol and then dried. Consequently, 5.5 g of crude crystals are obtained. The crude crystals are recrystallized from ethanol to obtain 5.0 g of the desired product.

Example 12:
1-[2-(3,4-Methylenedioxyphenyl)-2-hydroxyethyl]-4-(2-oxyindol-3-yl)-piperidine:

In this example, 0.3 g of sodium borohydride is added to a solution of 2.9 g of 1-(3,4-methylenedioxybenzoylmethyl)-4-(2-oxyindol-3-yl)-piperidine obtained in Example 11 in 50 ml of ethanol over a period of 30 minutes. After the addition, the mixture is stirred at room temperature for 2 hours and then concentrated. The residue is mixed with water to separate an oily substance, which is extracted with 50 ml of chloroform twice. The chloroform layer is washed with water and then dried. The dried layer is concentrated to dryness under reduced pressure and the residue is recrystallized from ethyl acetate to obtain 2.0 g of the desired product.

Example 13:
1-[2-(3,4-Dimethoxyphenyl)-2-oxo-1-methylethyl]-4-(2-oxyindol-3-yl)-piperidine:

In this example, 2.53 g of ω-bromo-3,4-dimethoxypropiophenone is added to a solution of 2.34 g of 4-(2-oxyindol-3-yl)-piperidine hydrochloride and 1.88 g of triethylamine in 40 ml of methanol. The mixture is stirred at room temperature for 24 hours. The resultant mixture is concentrated to dryness under reduced pressure, and the residue is mixed with water, stirred and then filtered. The crystals are washed with 20 ml of water and 5 ml of isopropyl alcohol and then dried to obtain 3.55 g of crude crystals. The crude crystals are recrystallized from isopropyl alcohol to obtain 3.0 g of the desired product.

Example 14:
1-[2-(3,4-Dimethoxyphenyl)-2-hydroxy-1-methylethyl]-4-(2-oxyindol-3-yl)-piperidine fumarate:

In this example, 1.0 g of sodium borohydride is added to a solution of 1.6 g of 1-[2-(3,4-dimethoxyphenyl)-2-oxo-1-methylethyl]-4-(2-oxyindol-3-yl)-piperidine obtained in Example 13 in 70 ml of methanol over a period of 30 minutes. The mixture is stirred at room temperature for 2 hours and then concentrated to dryness under reduced pressure. The residue is mixed with water and the resultant crystalline substance is separated by filtration. The crustalline substance is washed with water and then dried to obtain 1.49 g of crude crystals. The crude crystals are dissolved in 15 ml of isopropyl alcohol and then 0.42 g of fumaric acid is added thereto. The crystals deposited are separated by filtration and dried. The crude crystals are recrystallized from isopropyl alcohol to obtain 1.23 g of the desired product.

Example 15:
3-[1-(3,4-Methylenedioxybenzoylmethyl)-4-piperidylidene]-2-oxyindole:

In this example, 2.84 g of ω-bromo-3,4-methylenedioxyacetophenone is added to a solution of 2.5 g of 3-(4-piperidylidene)-2-oxyindole and 1.19 g of triethylamine in methanol. The mixture is stirred at room temperature for 7 hours. The reaction mixture is freed from the solvent by distillation. The residue is mixed with water, stirred and then filtered. The crystals are washed with 20 ml of water and 5 ml of ethanol and dried to obtain 3.83 g of a crude product. The crude product is recrystallized from ethanol to obtain 3.61 g of the desired product.

Example 16:
3-{1-[2-(3,4-Methylenedioxyphenyl)-2-hydroxyethyl]-4-piperidylidene}-2-oxyindole:

In this example, 4 g of 3-[1-(3,4-methylenedioxybenzoylmethyl)-4-piperidylidene]-2-oxyindole obtained in the same manner as that of Example 15 is dissolved in 300 ml of methylene chloride. To the solution, a solution of 8 g of diisobutyl aluminum hydride in 100 ml of methylene chloride is added dropwise at −25° C. over a period of 2 hours. The resultant mixture is further stirred at the same temperature for 5 hours. Then, 30 ml of methanol and subsequently 100 ml of water are added to the mixture, and the methylene chloride layer is separated. The methylene chloride layer is washed with 30 ml of water and then dried three times. The layer is freed from methylene chloride by distillation. The residue is mixed with 10 ml of ethyl acetate and stirred. The resultant crystals are separated by filtration and dried to obtain 4.0 g of a crude product. The crude product is recrystallized from methanol-methylene chloride to obtain 2.3 g of the desired product.

Example 17:
1-[2-(3,4-Methylenedioxyphenyl)-2-hydroxyethyl]-4-(2-oxyindol-3-yl)-piperidine:

In this example, 0.6 g of sodim borohydride is added to a solution of 2.9 g of 3-[1-(3,4-methylenedioxybenzoylmethyl)-4-piperidylidene]-2-oxyindole obtained in the same manner as that of Example 15 in 50 ml of ethanol over a period of one hour. After the addition, the mixture is stirred at room temperature for 2 hours and then concentrated. The residue is mixed with water and the oily substance separated is extracted with 50 ml of chloroform twice. The chloroform layer is washed with water and dried. The layer is freed from chlorofom by distillation. The residue is recrystallized from ethyl acetate to obtain 2.05 g of the desired product.

Example 18:
1-[2-(3,4-Dimethoxyphenyl)-2-oxo-ethyl]-4-(octahydro-2H-benzimidazol-2-one-1-yl)-piperidine:

In this example, 1.03 g of ω-bromo-3,4-dimethoxyacetophenone is added to a solution of 1.1 g of 4-(octahydro-2H-benzimidazol-2-one-1-yl)-piperidine hydrochloride and 810 mg of triethylamine in 10 ml of methanol. The mixture is stirred at room temperature for 2 hours. The reaction mixture is concentrated. The residue is mixed with water and the crystals formed are separated by filtration. The crystals are washed with water and then with isopropanol and subsequently dried. Consequently, 1.4 g of crude crystals are obtained. The crude crystals are recrystallized from 20 ml of ethanol to obtain 1.18 g of the desired product.

Compounds of Compound Nos. 38–40 can be prepared in a similar manner as that of this example.

Example 19:
1-[2-(3,4-Dimethoxyphenyl)-2-hydroxyethyl]-4-(octahydro-2H-benzimidazol-2-one-1-yl)-piperidine:

In this example, 720 mg of 1-[2-(3,4-dimethoxyphenyl)-2-oxo-ethyl]-4-octahydro-2H-benzimidazol-2-one-1-yl)-piperidine obtained by the procedure of Example 18 is suspended in 10 ml of methanol. To this suspension, 200 mg of sodium borohydride is added by portions at room temperature over a period of 30 minutes. After completion of the addition, the mixture is further stirred at room temperature for one hour and then concentrated. The residue is mixed with water and ethyl acetate and shaken. The organic layer is separated, washed with water and dried. The layer is concentrated to dryness under reduced pressure. The residue is mixed with a small amount of ether and stirred. The crystals formed are separated by filtration and dried to obtain 590 mg of crude crystals. The crude crystals are recrystallized from ethyl acetate to obtain 520 mg of the desired product.

The compounds of Compound Nos. 42–44 can be prepared in a similar manner to that of this example.

Example 20: (Example of preparing 10,000 5 mg-tablets)

| Compound 23 | 50 g |
|---|---|
| Magnesium stearate | 4 g |
| Crystalline cellulose | 746 g |

The above-described ingredients are mixed for 5 minutes by means of a mixer. The resulting mixed powder is made into 10,000 tablets of 6.0 mm in diameter, 2.5 mm in thickness, and 80 mg in weight using a tablet-making machine (Model HU-37; made by Kikusui Seisakusho) equipped with a pestle having a plane surface and round corners.

Example 21: (Example of preparing a powder)

| Compound 15 | 110 g |
|---|---|
| Lactose | 890 g |

The above-described ingredients are mixed for 10 minutes using a mixer to obtain a uniform mixture (powder).

Reference Example 1:
1-Benzyl-4-(2-aminoanilinopiperidine trihydrochloride:

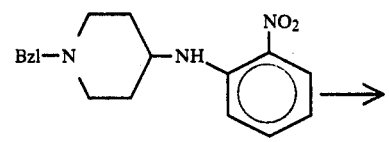

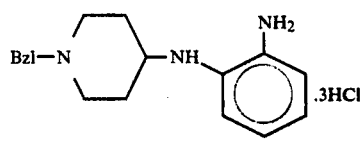

In this reference example, 600 mg of 1-benzyl-4-(2-nitroanilino)-piperidine is dissolved in methanol. The solution is mixed with 60 mg of 5% palladium carbon and stirred at 30°–32° C. in the atmosphere of hydrogen under the atmospheric pressure. The stirring is stopped after 2 hours and 30 minutes, and the catalyst is removed by filtration. The filtrate is mixed with 1 ml of a solution of 215 mg of hydrogen chloride gas in 1 ml of methanol and then concentrated. The residue is mixed with ether, filtered and dried to obtain 640 mg of the desired product as a powder.

Infrared absorption spectrum (KBr): 1625, 1280 cm$^{-1}$

| Elementary analysis (%) C$_{18}$H$_{26}$Cl$_3$N$_3$ | | | |
|---|---|---|---|
| | C | H | N |
| Calculated | 55.32 | 6.71 | 10.75 |
| Found | 55.22 | 6.75 | 10.68 |

Reference Example 2:
1-Benzyl-4-(1H-benzotriazol-1-yl)-piperidine:

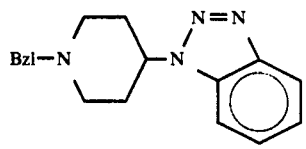

In this reference example, 2.0 g of 1-benzyl-4-(2-aminoanilino)-piperidine trihydrochloride obtained in the same manner as that of Reference Example 1 is dissolved in 30 ml of water and the solution is cooled to 0° C. To the cooled solution, 5 ml of a solution of 360 mg of sodium nitrite in 5 ml of water is added dropwise under the current of nitrogen gas over a period of 30 minutes. After completion of the dropwise addition, the reaction mixture is stirred at 0°–5° C. for one hour and then adjusted to pH 10.7. The reaction mixture is extracted with 30 ml of chloroform three times. The chloroform layer is washed with water and dried. The chloroform layer is concentrated to dryness under reduced pressure. The residue is subjected to silica gel chromatography [Wako Gel C-200, 150 ml, with a chloroform-methanol (10:1) as the eluent]. The eluate is concentrated to obtain 0.71 g of the desired product.

Melting point: 110°–111° C.

Infrared absorption spectrum (KBr): 1461, 1140, 1083 cm$^{-1}$

| Elementary analysis (%): C$_{18}$H$_{20}$N$_4$ | | | |
|---|---|---|---|
| | C | H | N |
| Calculated | 73.94 | 6.90 | 19.16 |
| Found | 74.12 | 6.88 | 19.27 |

Reference Example 3:
4-(1H-benzotriazol-1-yl)-piperidine acetate:

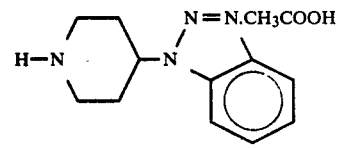

A solution of 8.76 g 1-benzyl-4-(1H-benzotriazol-1-yl)-piperidine obtained in the same manner as that of Reference Example 2 in 200 ml of methanol is mixed with 9.0 g of acetic acid and 20 g of 5% palladium carbon and shaken in the atmosphere of hydrogen at 50° C. under the initial pressure of 5 atmosphere. The reaction mixture is filtered and the filtrate is concentrated. The residue is recrystallized from ethyl acetate to obtain 8.6 g of the desired product.

Melting point: 132.5°–135.5° C.

IR (KBr): 1583, 1175 cm$^{-1}$

| Elementary analysis (%): $C_{11}H_{14}N_4 \cdot C_2H_4O_2$ | | | |
|---|---|---|---|
| | C | H | N |
| Calculated | 59.53 | 6.92 | 21.36 |
| Found | 59.31 | 6.97 | 21.62 |

Reference Example 4:
1-Benzyl-4-[N-(2-nitrophenyl)-N-acetylamino]-piperidine hydrobromide:

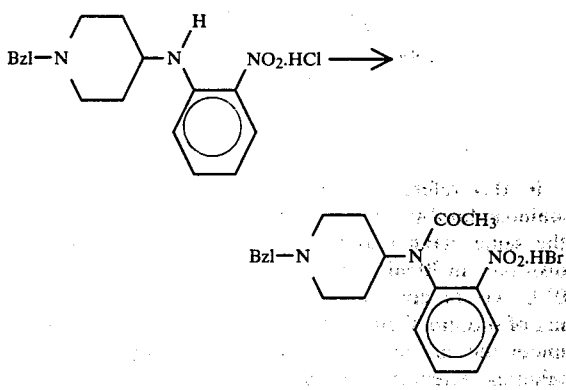

In this reference example, 1.67 g of 1-benzyl-4-(2-nitroanilino)-piperidine hydrochloride is suspended in 30 ml of dioxane. The suspension is mixed with 13 ml of acetyl bromide and refluxed for 4 hours. The resultant reaction mixture is cooled and then the deposited crystals are separated by filtration. The crystals are washed with ether and then dried to obtain 1.96 g of crude crystals. The crude crystals are recrystallized from 25 ml of ethanol to obtain 1.33 g of the desired product.
Melting point: 253°–255° C.
IR (KBr): 1665, 1658, 1530, 1378 $cm^{-1}$

| Elementary analysis (%): $C_{20}H_{24}BrN_3O_3$ | | | |
|---|---|---|---|
| | C | H | N |
| Calculated | 55.31 | 5.57 | 9.67 |
| Found | 55.41 | 5.54 | 9.38 |

Reference Example 5:
4-(2-Methyl-benzimidazol-3-yl)-piperidine:

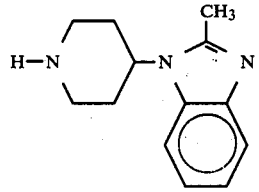

In this reference example, 14.8 g of 1-benzyl-4-[N-(2-nitrophenyl)-N-acetylamino]-piperidine hydrobromide obtained in the same manner as that of Refernce Example 4, 250 ml of methanol and 1.0 g of 5% palladium carbon are mixed and stirred at room temperature under the atmospheric pressure in the current of hydrogen for 12 hours. The resultant reaction mixture is filtered. The filtrate is mixed with 29 ml of concentrated hydrochloric acid and stirred overnight. The reaction solution is concentrated and the residue is dissolved in 50 ml of water. The solution is adjusted to pH 11.0 with 1 N aqueous sodium hydroxide. The solution is extracted with 50 ml of chloroform three times, and the extract is washed with 20 ml of a saturated aqueous sodium chloride and dried. The extract is freed from the solvent by distillation. The residue is mixed with n-hexane and stirred for crysallization. The crystals are separated by filtration, recrystallized from a mixed solvent of n-hexane and ethanol to obtain 6.7 g of 4-(2-methyl-benzimidazol-3-yl)-piperidine.
Melting point: 130°–132° C.
IR (KBr): 1468 $cm^{-1}$

| Elementary analysis (%): $C_{13}H_{17}N_3$ | | | |
|---|---|---|---|
| | C | H | N |
| Calculated | 72.52 | 7.96 | 19.52 |
| Found | 72.33 | 8.01 | 19.62 |

Reference Example 6:
1-tert.-Butoxycarbonyl-4-(2-nitrophenylmethylamino)-piperidine

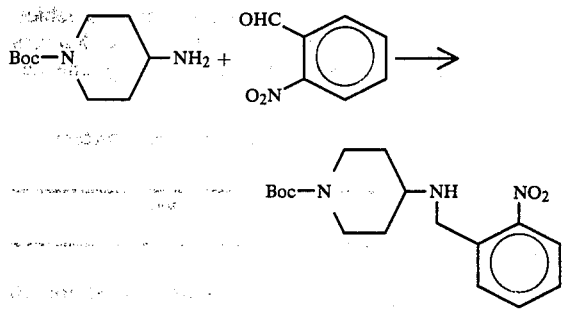

In this reference example, a solution of 36.1 g of 1-tert.-butoxycarbonyl-4-aminopiperidine and 27.3 g of 2-nitrobenzaldehyde in 100 ml of methanol is stirred at room temperature for one hour. Then, 6.8 g of sodium borohydride is added to the solution over a period of one hour. The mixture is stirred at room temperature for additional 2 hours and the solvent is distilled off under reduced pressure. Ethyl acetate and water are added to the residue and the mixture is stirred. The organic layer is separated, washed with saturated aqueous sodium chloride twice and dried. Ethyl acetate is distilled off to obtain 60.4 g of oily material as the residue. The residue is dissolved in 150 ml of isopropanol, 2.2 g of oxalic acid dihydrate is added thereto and the mixture is stirred. The resultant crystals are separated by filtration, washed with isopropanol and dried to obtain 61.1 g of oxalate of the desired compound. The oxalate is added to 2 l of water and pH of the mixture is adjusted to 11.0. The liberated oil material is extracted with ether (300 ml×3). The extract is washed with aqueous sodium chloride (200 ml×3) and dried. Ether is distilled off to obtain 41.1 g of the desired compound.
IR (Neat): 1680–1688, 1520
NMR (CDCl₃): 1.45(t-butyl), 4.07(—NHCH₂—)

A part of the above desired compound is converted to oxalate. The oxalate is recrystallized from isopropanol. Physical properties of the oxalate
Melting point: 194°–195° C.

| Elementary analysis (%): $C_{19}H_{27}N_3O_8$ | | | |
|---|---|---|---|
| | C | H | N |
| Calculated | 53.64 | 6.40 | 9.88 |
| Found | 53.60 | 6.65 | 9.81 |

Reference Example 7:
1-tert.-Butoxycarbonyl-4-(2-aminophenylmethylamino)-piperidine

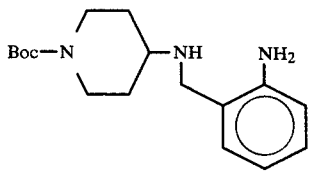

In this reference example, 40 g of 1-tert.-butoxycarbonyl-4-(2-nitrophenylmethylamino)-piperidine obtained in the same manner as that of Reference Example 6, 100 ml of ethanol, 60 ml of methanol and 4 g of palladium carbon are mixed. The mixture is shaken in an atmosphere of hydrogen at room temperature under 40-45 psi. The catalyst is filtered off and the filtrate is concentrated to obtain 35.1 g of oily material as the residue. The residue is crystallized with the addition of n-hexane to obtain 28.3 g of the crude crystals. Though the crude crystals are usable to the following reaction, a part of the crystals is recrystallized from n-hexane to obtain the desired compound.

Melting point: 79°-81° C.
IR (KBr): Disappearance of absorption at 1520 cm$^{-1}$

| Elementary analysis (%): $C_{17}H_{27}N_3O_2$ | | | |
|---|---|---|---|
| | C | H | N |
| Calculated | 66.85 | 8.91 | 13.76 |
| Found | 66.99 | 8.99 | 13.71 |

Reference Example 8:
1-tert.-Butoxycarbonyl-4-(2-cyanoimino-3,4-dihydro-1H-quinazolin-3-yl)-piperidine:

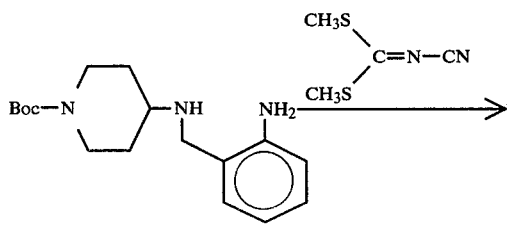

(Boc = tert-butoxycarbonyl)

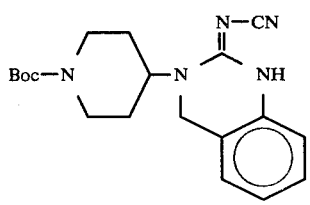

In this reference example, a solution of 28.0 g of 1-tert.-butoxycarbonyl-4-(2-aminophenylmethylamino)-piperidine obtained in the same manner as that of Reference Example 7, 2 g of dimethyl-N-cyanodithioiminocarbonate and 28 g of diazabicycloundecene in 150 ml of dioxane is heated at 63° C. for 10 hours. The solution is then cooled and the deposited crystals are separated by filtration. The crystals are dried and then recrystallized from methanol to obtain 18 g of 1-tert.-butoxycarbonyl-4-(2-cyanoimino-3,4-dihydro-1H-quinazolin-3-yl)-piperidine.

Melting point: 249°-250° C.
IR (KBr): 2300, 1688-1680, 1627, 1585 cm$^{-1}$

| Elementary analysis (%): $C_{19}H_{25}N_5O_2$ | | | |
|---|---|---|---|
| | C | H | N |
| Calculated | 64.20 | 7.09 | 19.71 |
| Found | 64.43 | 7.24 | 19.69 |

Reference Example 9:
4-(2-Cyanoimino-3,4-dihydro-1H-quinazolin-3-yl)-piperidine hydrochloride:

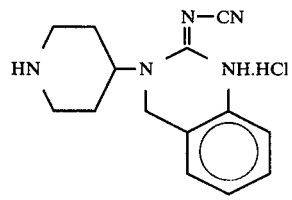

In this reference example, 13.0 g of the product obtained in Reference Example 8 is suspended in 100 ml of ethyl acetate. The suspension is cooled to 0° C. To the cooled suspension, 60 ml of ethyl acetate solution of 5.8 N HCl is added dropwise over a period of one hour. After the dropwise addition, the solution is further stirred at the same temperature for 30 minutes and then filtered. The resultant crystals are washed with 20 ml of ethyl acetate three times and dried to obtain 9.9 g of the desired compound.

Melting point: 260°-262° C. (decomposition)
IR (KBr): 2300, 1623, 1588 cm$^{-1}$

| Elementary analysis (%): $C_{14}H_{18}ClN_5$ | | | |
|---|---|---|---|
| | C | H | N |
| Calculated | 57.63 | 6.22 | 24.00 |
| Found | 57.61 | 6.33 | 23.87 |

Reference Example 10:
1-tert.-Butoxycarbonyl-4-[2-(methylthiocyanoiminomethyl)-aminoanilino]-piperidine:

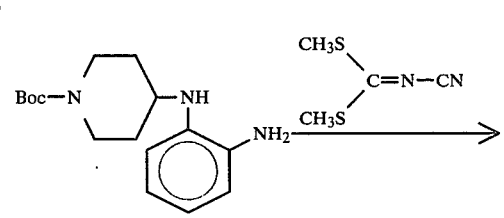

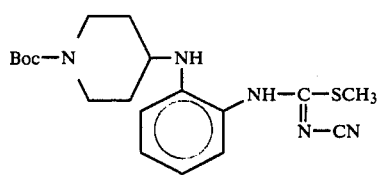

In this reference example, a solution of 1.0 g of 1-tert.-butoxycarbonyl-4-(2-aminoanilino)-piperidine, 1.0 g of dimethyl-N-cyanodithioiminocarbonate and 1.2 g of diazabicycloundecene in 50 ml of dioxane is heated to 80° C. for 7 hours. The solution is freed from dioxane by distillation under reduced pressure. The residue is mixed with water and ethyl acetate and shaken and then the organic layer is separated. The organic layer is washed with 10 ml of 0.6 N hydrochloric acid four times. The organic layer is further washed with a saturated aqueous sodium bicarbonate and water and then dried. The dried organic layer is concentrated to dryness under reduced pressure. The residue is subjected to silica gel chromatography (Wako Gel Q-200, 50 ml, with CHCl$_3$ as the eluent). The eluate is concentrated and the residual crystals are recrystallized from ethanol to obtain 0.6 g of the desired product.

Melting point: 169°–171° C.
IR (KBr): 2201, 1695, 1690, 1605, 1575 cm$^{-1}$

| Elementary analysis (%): C$_{19}$H$_{27}$N$_5$O$_2$S | | | |
|---|---|---|---|
| | C | H | N |
| Calculated | 58.59 | 6.99 | 17.98 |
| Found | 58.81 | 7.08 | 18.00 |

Reference Example 11:
1-tert.-Butoxycarbonyl-4-(2-cyanoimino-1H-benzimidazol-1-yl)-piperidine:

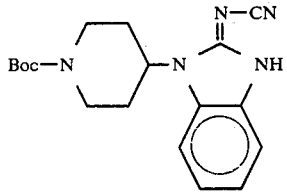

In this reference example, 2.48 g of the product obtained in the same manner as that of Reference Example 10 is suspended in 22 ml of methanol. This suspension is mixed with 2.1 g of mercuric acetate and stirred at room temperature for one hour. After completion of the reaction, the reaction solution is concentrated to dryness under reduced pressure. The residue is mixed with 30 ml of chloroform. The chloroform solution is washed four times with 10 ml of 0.32 N hydrochloric acid. The chloroform solution is further washed with 10 ml of a saturated aqueous sodium chloride four times and then dried. The solution is concentrated to dryness under reduced pressure and the residual crystals are recrystallized from ethanol to obtain 1.88 g of the desired product.

Melting point: 242°–243° C.
IR (KBr): 2198, 1699–1690, 1633, 1613 cm$^{-1}$

| Elementary analysis (%): C$_{18}$H$_{23}$N$_5$O$_2$ | | | |
|---|---|---|---|
| | C | H | N |
| Calculated | 63.32 | 6.79 | 20.52 |
| Found | 63.47 | 6.89 | 20.47 |

Reference Example 12:
4-(2-Cyanoimino-1H-benzimidazol-1-yl)-piperidine hydrochloride:

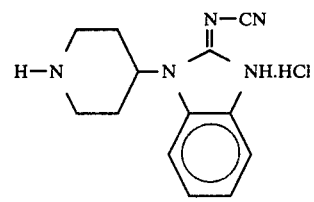

In this reference example, 18 g of the product obtained in the same manner as that of Reference Example 11 is suspended in 530 ml of ethyl acetate. To this suspension, 180 ml of ethyl acetate solution of 5.8 N HCl is added dropwise at room temperature over a period of 30 minutes. The mixture is stirred for 2 hours and then filtered. The resultant crystals are washed with 20 ml of ethyl acetate five times and then dried to obtain 13.3 g of the desired product.

Melting point: 273°–276° C. (decomposition
IR (KBr): 2195, 1630, 1601 cm$^{-1}$

| Elementary analysis (%): C$_{13}$H$_{16}$ClN$_5$ | | | |
|---|---|---|---|
| | C | H | N |
| Calculated | 56.22 | 5.81 | 25.21 |
| Found | 56.43 | 5.97 | 24.98 |

Reference Example 13:
3-[1-(tert.-Butoxycarbonyl)-4-piperidinylidene]-2-oxyindole:

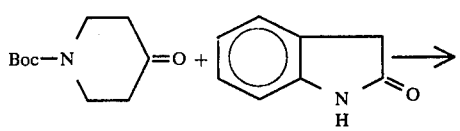

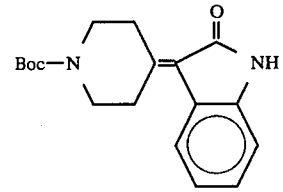

In this reference example, an ethanol solution of 2.4 g of ammonia is prepared by bubbling ammonia gas through 20 ml of ethanol. To this solution, 1.51 g of 1-tert.-butoxycarbonyl-4-piperidone and 1.01 g of oxyindole are added at 5° C. The resultant mixture is gradually heated to 70° C. The mixture is stirred at the same temperature for one hour and then freed from ammonia and the solvent by distillation under reduced pressure. The residue is mixed with a small amount of ethanol and then stirred. The crystals consequently deposited are separated by filtration and dried to obtain 1.7 g of crude crystals. The crude crystals are recrystallized from ethanol to obtain 1.62 g of the desired product.

Melting point: 204°–205° C.
IR (KBr): 1700, 1690, 1660 cm$^{-1}$

| Elementary analysis (%): $C_{18}H_{22}N_2O_3$ | | | |
| --- | --- | --- | --- |
| | C | H | N |
| Calculated | 68.77 | 7.05 | 8.91 |
| Found | 68.66 | 7.05 | 8.82 |

Reference Example 14:
3-(4-Piperidinylidene)-2-oxyindole:

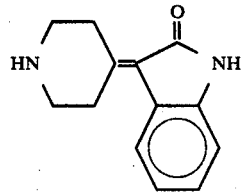

In this reference example, 7.5 g of 3-[1-(tert.-butoxycarbonyl)-4-piperidinylidene]-2-oxyindole obtained in the same manner as that of Reference Example 13 is added by portions to 25 g of trifluoroacetic acid which is cooled to 0° C. The resultant mixture is stirred at the same temperature for 2 hours and then concentrated to dryness under reduced pressure. The residue is mixed with water, and the resultant solution is adjusted to pH 10.6 with 0.1 N aqueous sodium hydroxide. The deposited crystals are separated by filtration and washed with water. The crude crystals are dried and then recrystallized from ethyl acetate to obtain 4.4 g of the desired product.

Melting point: 234°–238° C. (decomposition)
IR (KBr): 1697, 1680 cm$^{-1}$

| Elementary analysis (%): $C_{13}H_{14}N_2O$ | | | |
| --- | --- | --- | --- |
| | C | H | N |
| Calculated | 72.87 | 6.59 | 13.08 |
| Found | 72.59 | 6.60 | 12.81 |

Reference Example 15: 4-(2-Oxyindol-3-yl)-piperidine hydrochloride:

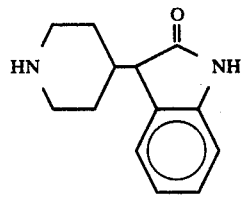

In this reference example, 0.5 g of 5% palladium carbon is added to a solution of 4.0 g of 3-(4-piperidinylidene)-2-oxyindole obtained in the same manner as that of Reference Example 14 in 200 ml of methanol. The mixture is stirred in the atmosphere of hydrogen under the atmospheric pressure for 10 hours. The mixture is filtered and the filtrate is concentrated. The residue is dissolved in 10 ml of ethanol. The crystals which are deposited therein by blowing dry hydrogen chloride gas into the solution are separated by filtration and then dried. The crude crystals are recrystallized from ethanol to obtain 3.8 g of the desired product.

Melting point: 284°–286° C. (decomposition)
IR (KBr): 1718 cm$^{-1}$

| Elementary analysis (%): $C_{13}H_{16}N_2O\cdot HCl$ | | | |
| --- | --- | --- | --- |
| | C | H | N |
| Calculated | 61.78 | 6.78 | 11.08 |
| Found | 61.65 | 6.86 | 11.04 |

Reference Example 16:
1-Benzyl-4-(2-nitro-cyclohexylamino)-piperidine:

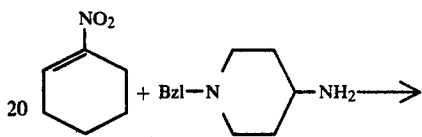

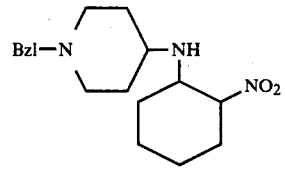

In this reference example, a solution of 16.6 g of 1-nitro-cyclohexene and 23 g of 1-benzyl-4-aminopiperidine in 150 ml of tetrahydrofuran is stirred overnight at room temperature. The reaction solution is filtered and the filtrate is concentrated. The residue is dissolved in 250 ml of 0.6 N hydrochloric acid. The solution is shaken with ether twice and then the water layer is separated. The water layer is adjusted to pH 9.5 with 1 N aqueous sodium hydroxide. The oily substance separated is extracted with 100 ml of ether three times. The extract is washed with water and then dried. The dried extract is concentrated under reduced pressure to obtain 30 g of an oily residue. This oily residue is subjected to silica gel chromatography (Wako Gel Q-200, with ethyl acetate as the eluent) to obtain 22.2 g of the desired product in an oily form.

IR (neat): 1545 cm$^{-1}$
NMR (CDCl$_3$): 0.75–3.4, 3.42, 3.85–4.5, 7.25 ppm

| Elementary analysis (%): $C_{18}H_{27}N_3O_2$ | | | |
| --- | --- | --- | --- |
| | C | H | N |
| Calculated | 68.11 | 8.57 | 13.24 |
| Found | 68.10 | 8.78 | 13.21 |

Reference Example 17:
1-Benzyl-4-(2-amino-cyclohexylamino)-piperidine:

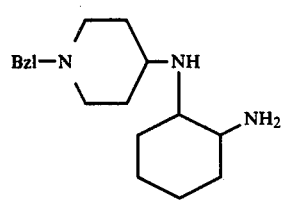

In this reference example, 1.0 g of 1-benzyl-4-(2-nitro-cyclohexylamino)-piperidine obtained in Reference Example 16 is dissolved in 25 ml of ethanol. Then, 1.0 g of a Raney-nickel catalyst is added thereto and the mixture is stirred at room temperature in the atmosphere of hydrogen under the atmospheric pressure. The stirring is ceased when the solution has absorbed the theoretical amount of hydrogen, and the reaction solution is filtered. The filtrate is concentrated. Consequently, 0.89 g of 1-benzyl-4-(2-aminocyclohexylamino)-piperidine is obtained as the residue.

IR (neat): 1580, 1450–1422 cm$^{-1}$

Although this compound is in a free form, it can be converted into a crystalline hydrochloride by introducing hydrogen chloride gas into an ethanol solution of the compound.

The hydrochloride is recrystallized from methanol. The trihydrochloride of 1-benzyl-4-(2-amino-cyclohexylamino)-piperidine exhibits the following properties.

Melting point: 245°–247° C.

| Elementary analysis (%): $C_{18}H_{32}N_3Cl_3$ | | | |
|---|---|---|---|
| | C | H | N |
| Calculated | 54.48 | 8.13 | 10.59 |
| Found | 54.25 | 8.38 | 10.43 |

Reference Example 18:
1-Benzyl-4-(octahydro-2H-benzimidazol-2-one-1-yl)-piperidine:

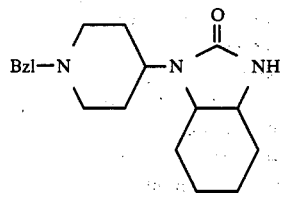

In this reference example, a solution of 631 mg of 1-benzyl-4-(2-amino-cylohexylamino)-piperidine in a free form obtained in Reference Example 17 and 550 mg of 1,1'-carbonyldiimidazole in 10 ml of acetonitrile is stirred at room temperature for 12 hours. The deposited crystals are separated by filtration, washed with acetonitrile and then dried to obtain 383 mg of crude crystals. The crude crystals are recrystallized from 34 ml of isopropanol to obtain 300 mg of the desired product.

Melting point: 192°–193° C.
IR (KBr): 1680 cm$^{-1}$

| Elementary analysis (%): $C_{19}H_{27}N_3O$ | | | |
|---|---|---|---|
| | C | H | N |
| Calculated | 72.80 | 8.68 | 13.41 |
| Found | 72.71 | 8.97 | 13.39 |

Reference Example 19:
4-(Octahydro-2H-benzimidazol-2-one-1-yl)-piperidine hydrochloride:

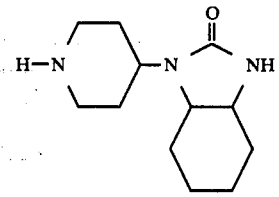

In this reference example, a solution of 6.1 g of 1-benzyl-4-(octahydro-2H-benzimidazol-2-one-1-yl)-piperidine obtained in the same manner as that of Reference Example 18 and 1 g of 5% palladium carbon in 100 ml of methanol, 100 ml of water and 20 ml of 12 N hydrochloric acid is shaken in the atmosphere of hydrogen under 4 to 5 atmosphere in an autoclave. The shaking is ceased when the absorption of hydrogen has been completed. The reaction mixture is subjected to filtration to remove the catalyst and the filtrate is concentrated. The residue is mixed with 20 ml of isopropanol and stirred to crystallize the reaction product. The crystals are dried and recrystallized from ethanol to obtain 3.9 g of the desired product.

Melting point: 300° C. (coloring)
IR (KBr): 1658, 1637 (shoulder) cm$^{-1}$

| Elementary analysis (%): $C_{12}H_{22}ClN_3O$ | | | |
|---|---|---|---|
| | C | H | N |
| Calculated | 55.48 | 8.54 | 16.18 |
| Found | 55.49 | 8.80 | 16.01 |

What is claimed is:
1. A compound represented by the formula:

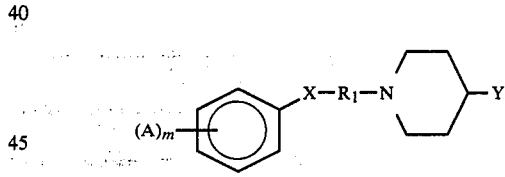

wherein A is lower alkoxy; m is 0 or an integer of 1–5, and when m is 2 or more, each A is the same group or each A is a different group and each A has the same definition as defined heretofore or two A groups may combine to form lower alkylenedioxy; X is carbonyl or hydroxymethylene; R$_1$ is a straight-chain alkylene having 1–4 carbon atoms with or without lower alkyl substituent(s); and Y is one of the following groups:

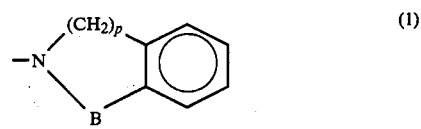

wherein p is 0 or 1, B is —N=N—,

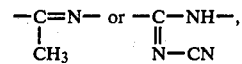

when p is 0, B is —N=N—, $$-\underset{\underset{CH_3}{|}}{C}=N- \text{ or } -\underset{\underset{N-CN}{\|}}{C}-NH-,$$

and when p is 1, B is $$-\underset{\underset{N-CH}{\|}}{C}-NH-,$$

and (2)

[cyclohexane-fused ring with —N—C(=O)—NH—]

or a pharmacologically acceptable acid addition salt thereof.

2. A compound according to claim 1 wherein $R_1$ is methylene with or without lower alkyl substitutent(s).

3. A compound according to claim 1 wherein said pharmacologically acceptable acid addition salt thereof is selected from the group consisting of hydrochloride, hydrobromide, hydroiodide, nitrate, sulfate, phosphate, acetate, benzoate, maleate, fumarate, succinate, tartrate, citrate, oxalate, glyoxylate, aspartate, methanesulfonate, ethanesulfonate, propanesulfonate, methanedisulfonate, α,β-ethanedisulfonate and benzenesulfonate.

4. A pharmaceutical composition having hypotensive activity which comprises at least one pharmaceutically acceptable carrier and an effective amount of a compound represented by the formula:

[structure: $(A)_m$—phenyl—X—$R_1$—N(piperidine)—Y]

wherein A is lower alkoxy; m is 0 or an integer of 1-5, and when m is 2 or more, each A is the same group or each A is a different group and each A has the same definition as defined heretofore or two A groups may combine to form lower alkylenedioxy; X is carbonyl or hydroxymethylene; $R_1$ is a straight-chain alkylene having 1-4 carbon atoms with or without lower alkyl substituent(s); and Y is one of the following groups:

$$-N\underset{B}{\overset{(CH_2)_p}{\diagup\!\!\diagdown}}\text{(benzene ring)} \quad (1)$$

wherein p is 0 or 1, B is —N=N—, $$-\underset{\underset{CH_3}{|}}{C}=N- \text{ or } -\underset{\underset{N-CN}{\|}}{C}-NH-,$$

when p is 0, B is —N=N—, $$-\underset{\underset{CH_3}{|}}{C}=N- \text{ or } -\underset{\underset{N-CN}{\|}}{C}-NH-,$$

and when p is 1, B is $$-\underset{\underset{N-CN}{\|}}{C}-NH-,$$

and (2)

[cyclohexane-fused ring with —N—C(=O)—NH—]

or a pharmacologically acceptable acid addition salt thereof.

* * * * *